(12) United States Patent
Zhu et al.

(10) Patent No.: US 9,101,731 B2
(45) Date of Patent: *Aug. 11, 2015

(54) VASCULAR WOUND CLOSURE DEVICE AND METHOD

(71) Applicant: Loma Linda University Medical Center, Loma Linda, CA (US)

(72) Inventors: Yong Hua Zhu, Redlands, CA (US); Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/923,235

(22) Filed: Jun. 20, 2013

(65) Prior Publication Data

US 2013/0281785 A1   Oct. 24, 2013

Related U.S. Application Data

(63) Continuation of application No. 12/862,402, filed on Aug. 24, 2010, now Pat. No. 8,491,628, which is a continuation of application No. 10/463,754, filed on Jun. 16, 2003, now Pat. No. 7,780,699, which is a (Continued)

(51) Int. Cl.
*A61B 17/03* (2006.01)
*A61M 25/00* (2006.01)
(Continued)

(52) U.S. Cl.
CPC ............ *A61M 25/00* (2013.01); *A61B 17/0057* (2013.01); *A61B 17/0206* (2013.01);
(Continued)

(58) Field of Classification Search
CPC ........... A61B 17/0057; A61B 17/0206; A61B 17/00491; A61B 2017/00623; A61B 2017/0065; A61B 2017/00601
USPC .................. 606/213–217; 604/13–18, 27, 28, 604/57–64
See application file for complete search history.

(56) References Cited

U.S. PATENT DOCUMENTS

| | | | |
|---|---|---|---|
| 1,064,307 A | 6/1913 | Fleming | |
| 3,518,993 A | 7/1970 | Blake | |

(Continued)

FOREIGN PATENT DOCUMENTS

| | | |
|---|---|---|
| CA | 2334226 | 4/2005 |
| CA | 2274066 | 2/2006 |

(Continued)

OTHER PUBLICATIONS

Angio-Seal, Homeostasis Puncture Closure Device Brochure, Sherwood Medical Co., Jun. 11, 1997.

(Continued)

*Primary Examiner* — Kathleen Holwerda
(74) *Attorney, Agent, or Firm* — Knobbe Martens Olson & Bear, LLP

(57) ABSTRACT

A method and apparatus for closing a vascular wound includes a guidewire and/or other surgical implement extending from the wound. A hemostatic material is advanced over the surgical implement and into contact with an area of the blood vessel surrounding the wound. The surgical implement is removed. Blood soaks the hemostatic material, and blood clotting is facilitated by the hemostatic agent within the material. A sealing layer of adhesive can be applied to the hemostatic material, confining the blood flow to the material. Thus, the vascular puncture wound is sealed by natural blood clot formation.

16 Claims, 31 Drawing Sheets

Related U.S. Application Data continuation-in-part of application No. 09/921,158, filed on Aug. 1, 2001, now Pat. No. 6,890,342.

(60) Provisional application No. 60/389,239, filed on Jun. 14, 2002, provisional application No. 60/222,525, filed on Aug. 2, 2000.

(51) Int. Cl.

| | | |
|---|---|---|
| *A61B 17/02* | (2006.01) | |
| *H04N 7/08* | (2006.01) | |
| *H04N 7/088* | (2006.01) | |
| *A61B 17/00* | (2006.01) | |
| *A61B 17/34* | (2006.01) | |
| *A61B 19/00* | (2006.01) | |

(52) U.S. Cl.
CPC ................ *H04N 7/08* (2013.01); *H04N 7/088* (2013.01); *A61B 17/00491* (2013.01); *A61B 17/3439* (2013.01); *A61B 2017/0065* (2013.01); *A61B 2017/00637* (2013.01); *A61B 2017/00654* (2013.01); *A61B 2017/00659* (2013.01); *A61B 2019/307* (2013.01)

(56) References Cited

U.S. PATENT DOCUMENTS

| | | | |
|---|---|---|---|
| 3,653,388 A | 4/1972 | Tenckhoff | |
| 3,677,244 A | 7/1972 | Hassinger | |
| 3,893,454 A | 7/1975 | Hagelin | |
| 4,166,469 A * | 9/1979 | Littleford | 607/122 |
| 4,306,562 A | 12/1981 | Osborne | |
| 4,317,445 A | 3/1982 | Robinson | |
| 4,412,832 A * | 11/1983 | Kling et al. | 604/164.05 |
| 4,451,256 A * | 5/1984 | Weikl et al. | 604/164.03 |
| 4,530,698 A | 7/1985 | Goldstein et al. | |
| 4,532,134 A | 7/1985 | Malette et al. | |
| 4,585,437 A | 4/1986 | Simms | |
| 4,622,970 A | 11/1986 | Wozniak | |
| 4,651,725 A | 3/1987 | Kifune et al. | |
| 4,738,658 A | 4/1988 | Magro et al. | |
| 4,772,266 A | 9/1988 | Groshong | |
| 4,821,719 A | 4/1989 | Fogarty | |
| 4,865,593 A | 9/1989 | Ogawa et al. | |
| 4,889,112 A | 12/1989 | Schachner et al. | |
| 4,890,612 A | 1/1990 | Kensey | |
| 4,900,303 A | 2/1990 | Lemelson | |
| 4,921,479 A | 5/1990 | Grayzel | |
| 4,961,729 A | 10/1990 | Vaillancourt | |
| 4,984,564 A | 1/1991 | Yuen | |
| 5,002,557 A | 3/1991 | Hasson | |
| 5,057,083 A | 10/1991 | Gellman | |
| 5,125,904 A | 6/1992 | Lee | |
| 5,129,882 A | 7/1992 | Weldon | |
| 5,152,279 A | 10/1992 | Wilk | |
| 5,176,128 A | 1/1993 | Andrese | |
| 5,176,129 A | 1/1993 | Smith | |
| 5,183,464 A | 2/1993 | Dubrul et al. | |
| 5,192,301 A | 3/1993 | Kamiya et al. | |
| 5,192,302 A | 3/1993 | Kensey et al. | |
| 5,222,974 A | 6/1993 | Kensey et al. | |
| 5,242,387 A | 9/1993 | Loughlin | |
| 5,250,033 A | 10/1993 | Evans et al. | |
| 5,257,979 A | 11/1993 | Jagpal | |
| 5,259,835 A | 11/1993 | Clark et al. | |
| 5,282,827 A | 2/1994 | Kensey et al. | |
| 5,290,310 A * | 3/1994 | Makower et al. | 606/213 |
| 5,292,309 A * | 3/1994 | Van Tassel et al. | 604/117 |
| 5,292,332 A | 3/1994 | Lee | |
| 5,300,065 A | 4/1994 | Anderson | |
| 5,306,254 A | 4/1994 | Nash et al. | |
| 5,306,259 A | 4/1994 | Fischell et al. | |
| 5,312,355 A | 5/1994 | Lee | |
| 5,318,542 A | 6/1994 | Hirsch et al. | |
| 5,320,639 A * | 6/1994 | Rudnick | 606/213 |
| 5,324,306 A | 6/1994 | Makower et al. | |
| 5,342,393 A | 8/1994 | Stack | |
| 5,350,399 A | 9/1994 | Erlebacher et al. | |
| 5,352,207 A | 10/1994 | Nussbaum | |
| 5,360,397 A | 11/1994 | Pinchuk | |
| 5,370,660 A | 12/1994 | Weinstein et al. | |
| 5,383,896 A | 1/1995 | Gershony et al. | |
| 5,383,899 A | 1/1995 | Hammerslag | |
| 5,391,183 A | 2/1995 | Janzen et al. | |
| 5,397,311 A | 3/1995 | Walker et al. | |
| 5,407,427 A | 4/1995 | Zhu et al. | |
| 5,411,520 A | 5/1995 | Nash et al. | |
| 5,417,699 A | 5/1995 | Klein et al. | |
| 5,419,765 A | 5/1995 | Weldon et al. | |
| 5,423,814 A | 6/1995 | Zhu et al. | |
| 5,431,639 A | 7/1995 | Shaw | |
| 5,437,631 A | 8/1995 | Janzen | |
| 5,443,484 A | 8/1995 | Kirsch et al. | |
| 5,445,597 A | 8/1995 | Clark et al. | |
| 5,458,571 A * | 10/1995 | Lampropoulos et al. | 604/509 |
| 5,480,380 A | 1/1996 | Martin | |
| 5,486,195 A | 1/1996 | Myers et al. | |
| 5,529,577 A | 6/1996 | Hammerslag | |
| 5,531,759 A | 7/1996 | Kensey et al. | |
| 5,536,251 A | 7/1996 | Evard et al. | |
| 5,545,178 A | 8/1996 | Kensey et al. | |
| 5,577,993 A | 11/1996 | Zhu et al. | |
| 5,620,461 A | 4/1997 | Muijs Van De Moer et al. | |
| 5,626,601 A | 5/1997 | Gershony et al. | |
| 5,643,318 A | 7/1997 | Tsukernik et al. | |
| 5,645,566 A | 7/1997 | Brenneman et al. | |
| 5,649,911 A | 7/1997 | Trerotola | |
| 5,649,959 A | 7/1997 | Hannam et al. | |
| 5,653,730 A | 8/1997 | Hammerslag | |
| 5,658,298 A | 8/1997 | Vincent et al. | |
| 5,662,681 A | 9/1997 | Nash et al. | |
| 5,665,106 A | 9/1997 | Hammerslag | |
| 5,665,107 A | 9/1997 | Hammerslag | |
| 5,674,231 A | 10/1997 | Green et al. | |
| 5,676,689 A * | 10/1997 | Kensey et al. | 606/213 |
| 5,725,551 A | 3/1998 | Myers et al. | |
| 5,728,114 A | 3/1998 | Evans et al. | |
| 5,728,132 A | 3/1998 | Van Tassel et al. | |
| 5,755,693 A | 5/1998 | Walker et al. | |
| 5,759,194 A | 6/1998 | Hammerslag | |
| 5,810,810 A | 9/1998 | Tay et al. | |
| 5,836,970 A | 11/1998 | Pandit | |
| 5,843,124 A | 12/1998 | Hammerslag | |
| 5,876,387 A | 3/1999 | Killian et al. | |
| 5,906,631 A | 5/1999 | Imran | |
| 5,910,155 A * | 6/1999 | Ratcliff et al. | 606/213 |
| 5,928,266 A | 7/1999 | Kontos | |
| 5,944,730 A | 8/1999 | Nobles et al. | |
| 5,971,956 A | 10/1999 | Epstein | |
| 6,004,341 A | 12/1999 | Zhu et al. | |
| 6,007,563 A | 12/1999 | Nash et al. | |
| 6,033,413 A | 3/2000 | Mikus et al. | |
| 6,048,358 A | 4/2000 | Barak | |
| 6,056,768 A | 5/2000 | Cates et al. | |
| 6,060,461 A | 5/2000 | Drake | |
| 6,110,184 A | 8/2000 | Weadock | |
| 6,155,265 A | 12/2000 | Hammerslag | |
| 6,159,178 A | 12/2000 | Sharkawy et al. | |
| 6,197,042 B1 | 3/2001 | Ginn et al. | |
| 6,198,016 B1 | 3/2001 | Lucast et al. | |
| 6,277,140 B2 | 8/2001 | Ginn et al. | |
| 6,287,322 B1 | 9/2001 | Zhu et al. | |
| 6,287,323 B1 | 9/2001 | Hammerslag | |
| 6,315,753 B1 | 11/2001 | Cragg et al. | |
| 6,325,789 B1 | 12/2001 | Janzen et al. | |
| 6,346,093 B1 | 2/2002 | Allman et al. | |
| 6,371,974 B1 | 4/2002 | Brenneman | |
| 6,391,048 B1 | 5/2002 | Ginn et al. | |
| 6,425,901 B1 | 7/2002 | Zhu et al. | |
| 6,461,364 B1 | 10/2002 | Ginn et al. | |
| 6,508,828 B1 | 1/2003 | Akerfeldt et al. | |
| 6,524,326 B1 | 2/2003 | Zhu et al. | |
| 6,530,896 B1 * | 3/2003 | Elliott | 604/60 |

(56) References Cited

U.S. PATENT DOCUMENTS

| | | | |
|---|---|---|---|
| 6,589,269 B2 | 7/2003 | Zhu et al. | |
| 6,613,070 B2 | 9/2003 | Redmond et al. | |
| 6,632,238 B2 | 10/2003 | Ginn et al. | |
| 6,649,162 B1 | 11/2003 | Biering et al. | |
| 6,808,509 B1 | 10/2004 | Davey | |
| 6,890,342 B2 | 5/2005 | Zhu et al. | |
| 6,964,675 B2 | 11/2005 | Zhu et al. | |
| 7,201,725 B1 | 4/2007 | Cragg et al. | |
| 7,303,552 B1 | 12/2007 | Chu et al. | |
| 7,331,981 B2 | 2/2008 | Cates et al. | |
| 7,780,699 B2* | 8/2010 | Zhu et al. | 606/213 |
| 7,931,628 B2 | 4/2011 | Zhu et al. | |
| 8,012,167 B2 | 9/2011 | Zhu et al. | |
| 8,491,628 B2* | 7/2013 | Zhu et al. | 606/213 |
| 2001/0004710 A1 | 6/2001 | Felt et al. | |
| 2001/0018598 A1 | 8/2001 | Cruise et al. | |
| 2002/0002386 A1 | 1/2002 | Ginn et al. | |
| 2002/0022822 A1 | 2/2002 | Cragg et al. | |
| 2002/0072768 A1 | 6/2002 | Ginn | |
| 2002/0077656 A1 | 6/2002 | Ginn et al. | |
| 2002/0077657 A1 | 6/2002 | Ginn et al. | |
| 2002/0147479 A1 | 10/2002 | Aldrich | |
| 2003/0023267 A1 | 1/2003 | Ginn | |
| 2003/0044380 A1 | 3/2003 | Zhu et al. | |
| 2003/0045893 A1 | 3/2003 | Ginn | |
| 2003/0050590 A1 | 3/2003 | Kirsch | |
| 2003/0050665 A1 | 3/2003 | Ginn | |
| 2003/0078598 A1 | 4/2003 | Ginn | |
| 2003/0109820 A1 | 6/2003 | Gross et al. | |
| 2003/0125654 A1 | 7/2003 | Malik | |
| 2003/0158577 A1 | 8/2003 | Ginn et al. | |
| 2003/0158578 A1 | 8/2003 | Pantages et al. | |
| 2003/0167050 A1 | 9/2003 | Prosl et al. | |
| 2004/0059348 A1 | 3/2004 | Geske et al. | |
| 2005/0085856 A1 | 4/2005 | Ginn | |
| 2005/0095275 A1 | 5/2005 | Zhu et al. | |
| 2005/0107826 A1 | 5/2005 | Zhu et al. | |
| 2005/0118238 A1 | 6/2005 | Zhu et al. | |
| 2005/0123588 A1 | 6/2005 | Zhu et al. | |
| 2005/0142172 A1 | 6/2005 | Kirsch et al. | |
| 2005/0209637 A1 | 9/2005 | Zhu et al. | |
| 2005/0240137 A1 | 10/2005 | Zhu et al. | |
| 2006/0064124 A1 | 3/2006 | Zhu et al. | |
| 2007/0123816 A1 | 5/2007 | Zhu et al. | |

FOREIGN PATENT DOCUMENTS

| | | |
|---|---|---|
| DE | 92/02738 | 10/1992 |
| EP | 0 482 350 A2 | 4/1992 |
| EP | 0 646 350 A1 | 4/1995 |
| EP | 0 493 810 B1 | 11/1995 |
| EP | 0 745 350 A1 | 12/1995 |
| EP | 0 955 900 B1 | 7/1997 |
| EP | 0 788 769 A1 | 8/1997 |
| EP | 0 818 178 A2 | 1/1998 |
| GB | 2142244 A | 1/1985 |
| GB | 2318295 A | 4/1998 |
| JP | H6-339483 | 12/1994 |
| JP | 8-322846 | 12/1996 |
| JP | H10-43311 | 2/1998 |
| JP | 11-128360 | 5/1999 |
| WO | WO 93/25148 | 12/1993 |
| WO | WO 94/21306 A1 | 9/1994 |
| WO | WO 95/05206 A2 | 2/1995 |
| WO | WO 96/24291 A1 | 8/1996 |
| WO | WO 97/20505 A1 | 6/1997 |
| WO | WO 98/24374 A1 | 6/1998 |
| WO | WO 99/20326 | 4/1999 |
| WO | WO 99/62405 A1 | 12/1999 |
| WO | WO 00/02488 A1 | 1/2000 |
| WO | WO 00/07640 A2 | 2/2000 |
| WO | WO 00/19912 A1 | 4/2000 |
| WO | WO 00/33744 A1 | 6/2000 |
| WO | WO 01/34238 A1 | 5/2001 |
| WO | WO 01/62159 A2 | 8/2001 |
| WO | WO 02/05865 A2 | 1/2002 |
| WO | WO 02/09591 A2 | 2/2002 |
| WO | WO 03/008002 A1 | 1/2003 |
| WO | WO 03/008003 A1 | 1/2003 |
| WO | WO 03/105697 A1 | 12/2003 |
| WO | WO 2004/110284 A1 | 12/2004 |
| WO | WO 2007/044510 | 4/2007 |

OTHER PUBLICATIONS

Gershony, Gary, M.D., A Novel Femoral Access Site Closure Device: Duet, Early European Clinical Trials, Los Angeles Cardiology Associates, Seminar, Coronary Interventions, Oct. 16-18, 1997.

Medafor, Inc. Adds Two Management Team Members, Press Release, Jun. 7, 2001. http://www.medafor.com/news0601.html.

"Microporous Polysaccharide Hemospheres Provides Effective Topical Hemostasis in a Human Modified Bleeding Time Incision Model" by Medafore, Sep. 2002.

* cited by examiner

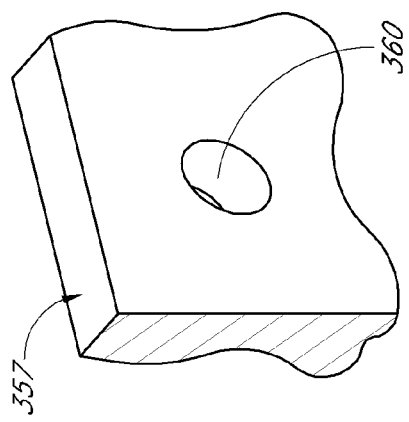
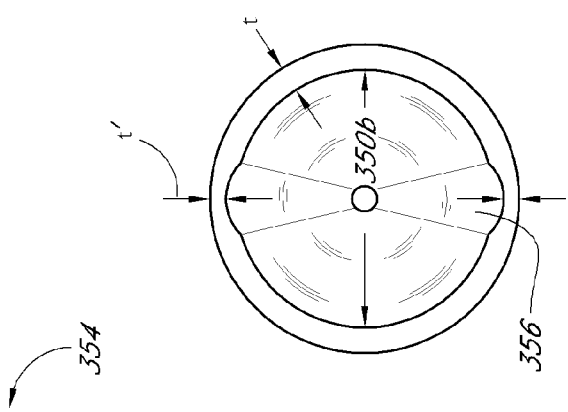
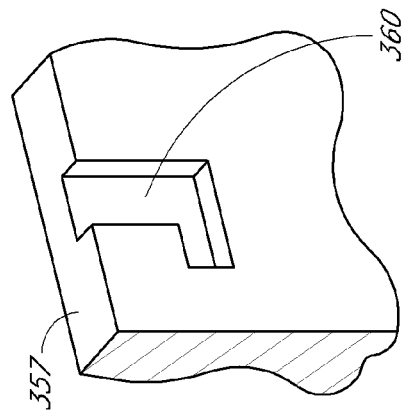

VASCULAR WOUND CLOSURE DEVICE AND METHOD

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 12/862,402 filed Aug. 24, 2010, which is a continuation of U.S. application Ser. No. 10/463,754 filed Jun. 16, 2003, now U.S. Pat. No. 7,780,699. U.S. application Ser. No. 10/463,754 claims priority to U.S. Provisional Application No. 60/389,239 filed on Jun. 14, 2002. U.S. application Ser. No. 10/463,754 is a continuation-in-part of U.S. application Ser. No. 09/921,158 filed on Aug. 1, 2001, now U.S. Pat. No. 6,890,342, which claims priority to U.S. Provisional Application No. 60/222,525 filed on Aug. 2, 2000.

FIELD OF THE INVENTION

The present invention generally relates to a system that facilitates closure of openings in blood vessels. More specifically, the present invention delivers a material adjacent a vessel.

BACKGROUND OF THE INVENTION

In many medical procedures, it is necessary to locate an opening in tissue so that some form of treatment, diagnosis or revision, can be applied to that opening. For example, in order to perform transluminal balloon angioplasty, an opening must be created in an artery in order to insert a balloon. This opening must later be closed.

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, it is also less expensive because of the shorter hospital stay and shorter recovery time.

Transluminal balloon angioplasty is performed by first inserting a hollow needle through the skin and surrounding tissues and into the patient's femoral artery. A guidewire is advanced through the hollow needle and into the artery, then along the patient's vasculature toward the site of the blocked blood vessel or heart valve to be treated. X-ray imaging is used to help move the guidewire through the vascular system and into position just past the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

Angiography, which is used to detect diseases that alter the appearance of blood vessels, is performed in a similar manner. A hollow needle is first inserted into the femoral artery and a guidewire is inserted through the needle and into the affected blood vessel. A catheter is threaded over the guidewire and into the blood vessel. X-ray imaging is used to guide the catheter to a desired position. Contrast medium is then injected, and a rapid sequence of x-ray pictures are taken so that blood flow along the affected vessel can be studied. The catheter and guidewire are later removed from the patient's body.

After the catheter used during angioplasty or angiography is removed, the puncture wound in the femoral artery must be closed and the bleeding through the puncture site in the artery stopped. Currently, ice packs and/or pressure are applied to the area surrounding the wound for a period lasting up to several hours in an attempt to stop the bleeding. There exists, however, a significant chance that the wound will reopen and begin bleeding again when the patient moves. Another possible complication is the development of a false aneurysm, which increases the risks of both infection and reopening.

Although efforts have been made to close the puncture wound using staples, clips, collagen plugs, and sutures, they have been unsuccessful, largely due to the inability to see the puncture wound in the femoral artery, and also because of the difficulty of controllably modifying the artery in the limited space provided.

Other wounds in the vasculature of a patient can also be difficult to see, and are thus difficult to locate, access and close. Thus, a device and method to facilitate locating and closing of such wounds in the vasculature of a patient would be extremely beneficial. A device having the ability to consistently and reliably locate, isolate and close the puncture wound would eliminate the prolonged bleeding currently associated with such wounds.

SUMMARY OF THE INVENTION

Accordingly, there is a need in the art for a device and method for precisely locating a blood vessel wound and sealing the wound.

In accordance with one aspect, the present invention includes an assembly for closing a vascular wound. A catheter of the assembly has a proximal end, a distal end and a lumen. At least one indicator hole is formed through a wall of the catheter proximal a distal end of the catheter. A retractor of the assembly has at least two retractor arms movably connected to each other. The arms are configured to be moved between an open position and a closed position. Each of the retractor arms defines an inner surface, which the inner surfaces define a channel through the retractor arms when the arms are in the closed position. The channel is figured to receive the catheter. At least a portion of the channel is sized to engage the surface of the catheter to hold the catheter in a fixed position relative to the closed arms. At least a second portion of the channel is configured to define a space between the inner surface and the catheter.

In accordance with another aspect, an assembly for closing a vascular wound is provided. The assembly includes a delivery tube configured to accommodate a hemostatic material therewithin, which delivery tube has a proximal end and a distal end. An apparatus is configured to position the distal end of the delivery tube adjacent the vascular wound. A pusher member has a distal portion configured to fit at least partially through the proximal end of the delivery tube. A portion of the pusher has a diameter larger than the diameter of at least a portion of the delivery tube.

For purposes of summarizing the preferred embodiments and the advantages achieved over the prior art, certain embodiments and advantages have been described herein above. Of course, it is to be understood that not necessarily all such advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

The embodiments discussed above and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 31 shows a cross section of the delivery tube of FIG. 30 taken along line 31-31.

FIG. 32 shows a wall portion of the delivery tube of FIG. 30 having a detent catch coupling portion.

FIG. 34 shows a wall portion of another embodiment of a delivery tube having a j-lock coupling portion.

DETAILED DESCRIPTION OF THE PREFERRED EMBODIMENT

The present apparatus and method is especially useful for closing vascular puncture wounds that are difficult to access and/or visualize. It is difficult to directly and accurately modify a wound in a blood vessel in order to close such wounds. Additionally, there are pitfalls associated with directly modifying the blood vessel. For example, since the clinician cannot see the wound, it is difficult to correctly place closure media such as sutures, staples, or clips. Incorrect placement of such closure media likely results in inadequate closure; the puncture wound remains open, perhaps without the clinician being aware. Additionally, incorrect placement of closure media may cause permanent damage to the vessel, including tearing and additional puncture wounds. Further, if closure media extends through the wound and into the blood flow, this media can increase the likelihood of thrombus formation or could introduce potentially toxic substances into the bloodstream. Of course, closure media inadvertently released into the bloodstream could lead to serious blood vessel blockage complications.

Figure 1:
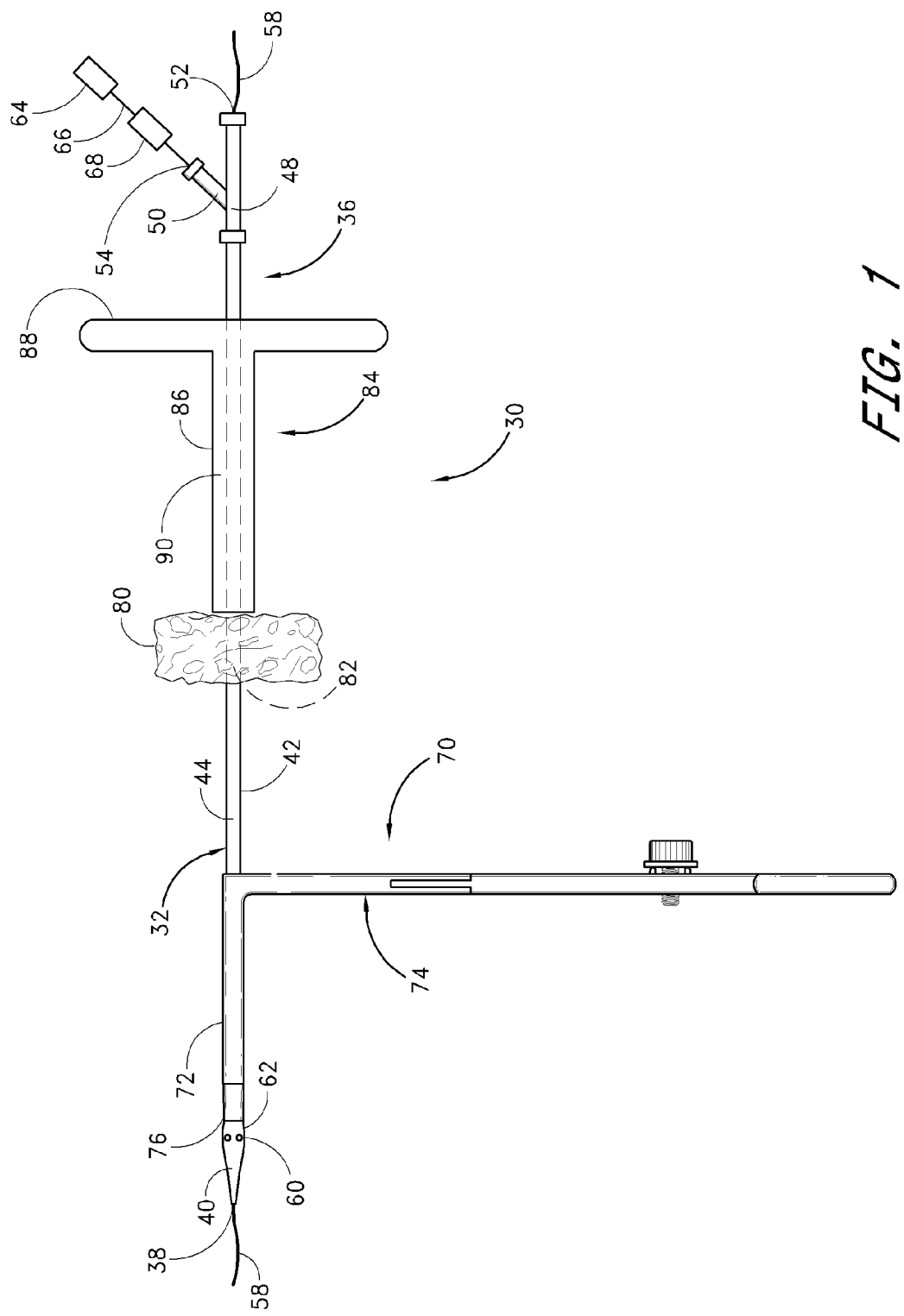
FIG. 1 is a side view of an embodiment of a vascular closure apparatus shown assembled and ready for use.

With reference to FIG. 1, a vascular wound closure assembly 30 includes an elongate catheter 32 having a distal end 34 and a proximal end 36 of the catheter 32. A distal opening 38 is formed through the distal end 34 of the catheter 32 and opens along a longitudinal axis of the catheter 32. The catheter 32 includes a tapered tip 40 at the distal end 34. An elongate main body 42 of the catheter 32 is disposed proximal the tapered tip 40. Preferably the main body 42 has a substantially uniform diameter along its length. A lumen 44 extends longitudinally within the catheter 32 from the distal opening 38 to the proximal end 36.

A connector portion 46 is provided on the proximal end 36. The connector portion 46 includes a main lumen 48 and a secondary lumen 50. The main lumen 48 extends along the longitudinal axis of the catheter 32 and is coextensive with the catheter lumen 44. The secondary lumen 50 extends outwardly from the main lumen 48, but communicates with the main lumen 48 and the catheter lumen 44. A proximal opening 52 is provided at the proximal end of the main lumen 48 and, like the distal opening 38, opens along the longitudinal axis. A secondary opening 54 opens into the secondary lumen 50.

The distal and proximal openings 38, 52 are sized and adapted to accommodate a guidewire 58 such as the guidewire used in angioplasty and other vascular surgeries. As such, the guidewire 58 can be threaded through the catheter 32 and the catheter can be advanced over the guidewire 58.

Holes 60 are formed through a side wall of the catheter 32 near the distal end 34 of the catheter 32. Preferably, at least two holes 60 are provided. All of the holes 60 preferably are disposed substantially the same distance from the distal end 34 of the catheter 32. Preferably, a raised portion 62 of the catheter 32 is provided in the region around the holes 60, which region is proximal of the tip 40 and distal of the main body 42. At the raised portion 62, the catheter 32 has an outer diameter that is slightly larger than the outer diameter throughout the catheter main body 42.

With continued reference to FIG. 1, a vacuum or other source of suction 64 is provided and communicates, through tubing 66, with the secondary lumen 50 of the catheter connector portion 46. Thus, a vacuum is drawn through the catheter lumen 44. Preferably, the distal and proximal openings 38, 52, which accommodate the guidewire 58, are sized so that the guidewire 58 substantially plugs the openings; thus, the vacuum is drawn through the holes 60. A viewing port 68 is arranged between the source of suction 64 and the catheter 32. The viewing port 68 is configured to allow a clinician to view the material that is drawn by suction through the holes 60 and through the catheter lumen 44. The viewing port 68 will be discussed in more detail below.

Figure 2:
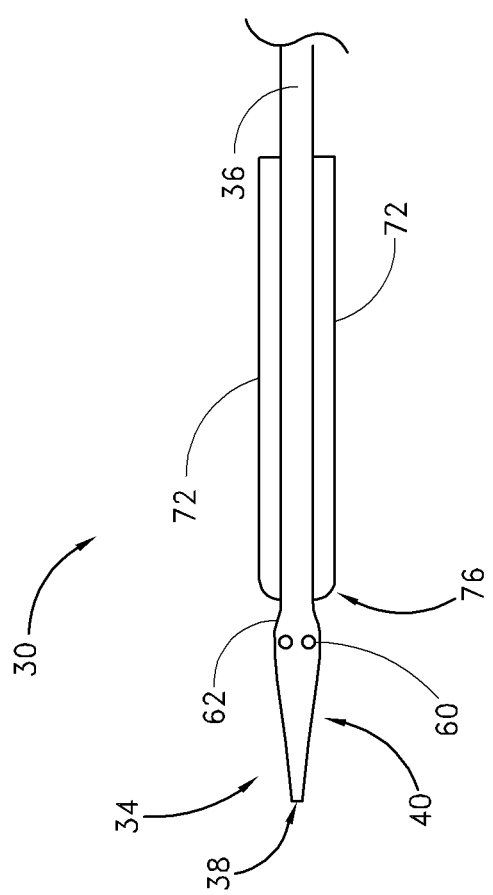
FIG. 2 is a side view of a distal portion of the apparatus of FIG. 1.

With reference to FIGS. 1 and 2, a retractor 70 preferably is mounted on the catheter 32. The retractor 70 includes opposing elongate retractor arms 72 that are aligned longitudinally on the catheter 32. A retractor body 74 is configured to selectively open and close the retractor arms 72 when operated by a clinician. The elongate retractor arms 72 of the retractor 70 are positioned on the catheter 32 so that distal ends 76 of the arms are positioned proximal of the catheter holes 60 a distance that is at least the same as the width of an artery wall, preferably at least about 0.5 to 2 millimeters.

It is to be understood that the present device can include structure that is somewhat different than the particular structure shown in FIGS. 1 and 2. For example, other catheter and retractor structures can appropriately be used. For example, some acceptable catheter and retractor embodiments are presented in U.S. application Ser. No. 09/325,982, filed on Jun. 4, 1999, now U.S. Pat. No. 6,287,322, which is hereby incorporated by reference in its entirety.

With reference again to FIG. 1, a hemostatic member 80 is arranged on the catheter 32 proximal of the retractor 70. As will be discussed in more detail below, the hemostatic member comprises a material that is made of or includes a hemostatic agent. The hemostatic agent is adapted to aid blood clotting. In one embodiment, the hemostatic member 80 comprises a sponge or sponge-like material. In this description, the term sponge is intended to be a broad term that is used in accordance with it ordinary meaning and refers to, without limitation, a material that is at least partially porous and is adapted to allow at least some blood to flow into and within the material so as to soak the material with blood. For example, a sponge may include a natural or artificial sponge, a woven or non-woven cloth, a fibrous puff or the like. Additionally, a sponge may comprise a material that soaks up at least a portion of blood that may come in contact with the material, or may comprise a material that doesn't soak up blood.

For purposes of this description, the hemostatic member 80 is referred to as the sponge 80. However, it is to be understood that use of the term "sponge" does not limit the scope of materials that can be used as the hemostatic member. In fact, any material that aids or facilitates blood clotting can be used as the hemostatic member.

Throughout this description, the term hemostatic agent is used as a broad term in its ordinary sense and refers to, without limitation, an agent that promotes blood clotting. Such an agent may take many forms, including liquid, powder, beads, etc. and can include or be combined with a carrier. The term hemostatic material is also used in this description as a broad term used in its ordinary sense. It refers to, without limitation, any material having properties that promote blood clotting. Thus, hemostatic material can include a hemostatic agent taken alone or in combination with a carrier that is formed separately from the agent. The term hemostatic material includes hemostatic sponges.

Preferably, the sponge 80 extends circumferentially around the catheter main body 42, and is arranged so that it can be slid longitudinally along the catheter 32. Most preferably, the catheter 32 extends through a passageway 82 through the sponge 80. The passageway 82 is formed as the catheter 32 is forced through the sponge 80.

Figure 3:
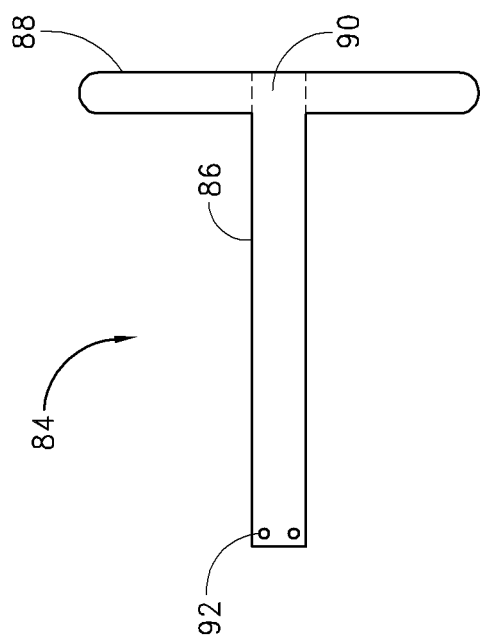
FIG. 3 is a side view of a push member having features in accordance with the present invention.

A push member 84 is also arranged on the catheter 32 proximal of the sponge 80. With reference also to FIG. 3, the push member 84 comprises a body portion 86 and a proximal handle portion 88. An elongate lumen 90 is formed through the body portion 86. As shown in FIG. 1, the lumen 90 preferably encircles the catheter 32 so as to allow the push member 84 to slide relative to the catheter 32. A plurality of holes 92 are formed through the body portion 86 at a point near the distal end of the push member 84.

As will be discussed in more detail below in connection with FIG. 4, the vascular wound closure assembly 30 enables a clinician to precisely locate a subcutaneous vascular wound "w", access the wound w, and deliver the hemostatic sponge 80 to the wound site. The hemostatic sponge 80 includes a hemostatic agent that helps facilitate closure of the wound w.

In order to properly apply the hemostatic sponge 80, the vascular closure assembly 30 first precisely locates and provides access to the vascular wound w. It is to be understood that the present method and apparatus can be used to close various vascular and other wounds. FIGS. 1-11, and the accompanying discussion, present an example using an embodiment to close a puncture wound w in a patient's femoral artery 94.

With specific reference to FIGS. 1, 2, 4 and 5, in order to precisely locate and provide access to a femoral artery puncture wound w, the catheter 32 is first threaded over a guidewire 58 that has been previously inserted into the patient's femoral artery 94 through the puncture wound w. The lumen 44 is attached to the source of suction 64 and the assembly 30 is advanced over the guidewire 58 through a patient's tissue 96 so that the distal tip 40 of the catheter 32 extends through the vascular puncture wound w.

As the assembly 30 is advanced, the source of suction 64 draws bodily fluids through the holes 60. The fluids pass through the viewing port 68, which allows the clinician to identify the fluids being withdrawn. The viewing port 68 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 32 is formed of a transparent material so that the clinician becomes aware as soon as blood begins to be drawn through the catheter.

Figure 4:
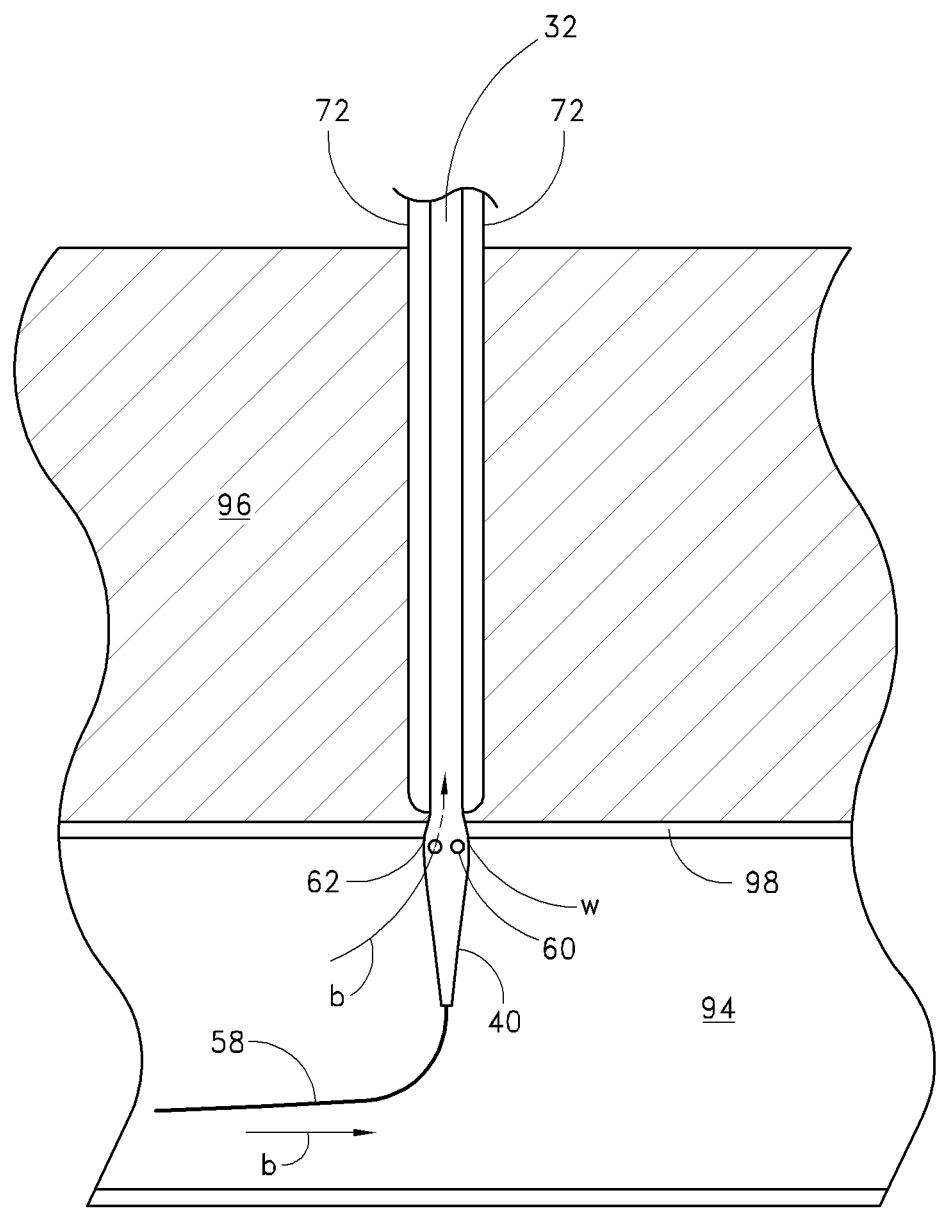
FIG. 4 shows the apparatus of FIG. 1 advanced over a guidewire into a blood vessel of a patient.
Figure 5:
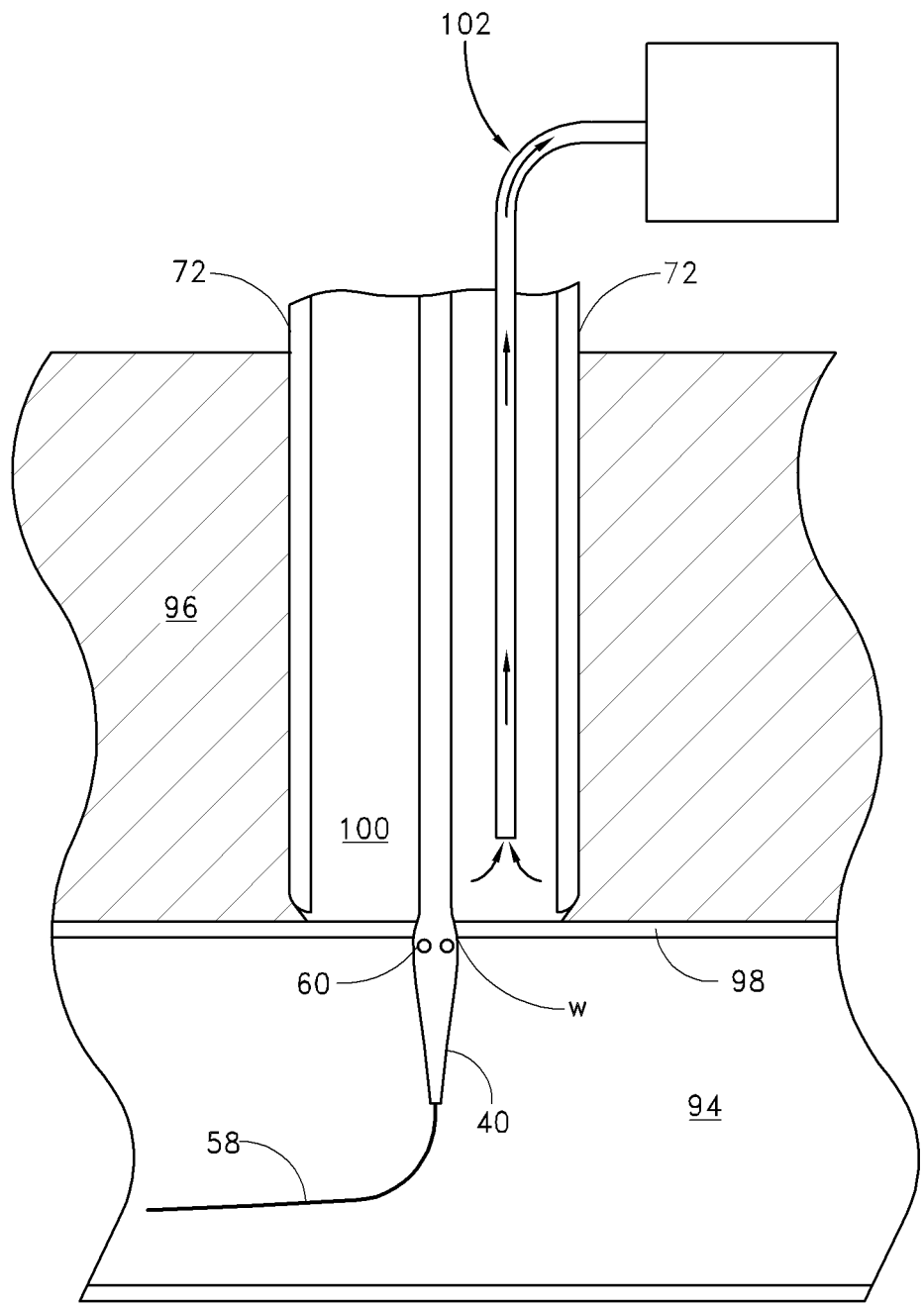
FIG. 5 shows the arrangement of FIG. 4 with the retractor arms open and a suction tool in use.

When the holes 60 pass the artery wall 98 and enter the blood vessel 94, as shown in FIG. 4, blood "b" begins to be drawn through the holes 60 into the catheter 32 and is conducted past the viewing port 68. Thus, when blood b is observed in the viewing port 68, the clinician will know that the holes 60 have just passed into the puncture wound w and that the distal ends 76 of the retractor arms 72 are thus positioned adjacent the outer wall 98 of the artery 94, preferably within about 2 mm of the artery wall 98. The retractor arms 72 are then separated as shown in FIG. 5, thus drawing surrounding tissue 96 away from the wound w and creating a field 100 around the puncture wound w. The catheter 32 remains disposed partially within the puncture wound w, effectively plugging the wound and preventing blood from flowing through the wound. The raised portion 62 flexes the edges of the wound w to enhance the seal between the catheter 32 and the puncture wound edges.

With continued reference to FIG. 5, a suction tool 102 can be used to clear away bodily fluids and other matter that may be within the field 100 and to clean the wall 98 of the blood vessel 94 adjacent the puncture wound w.

Figure 6:
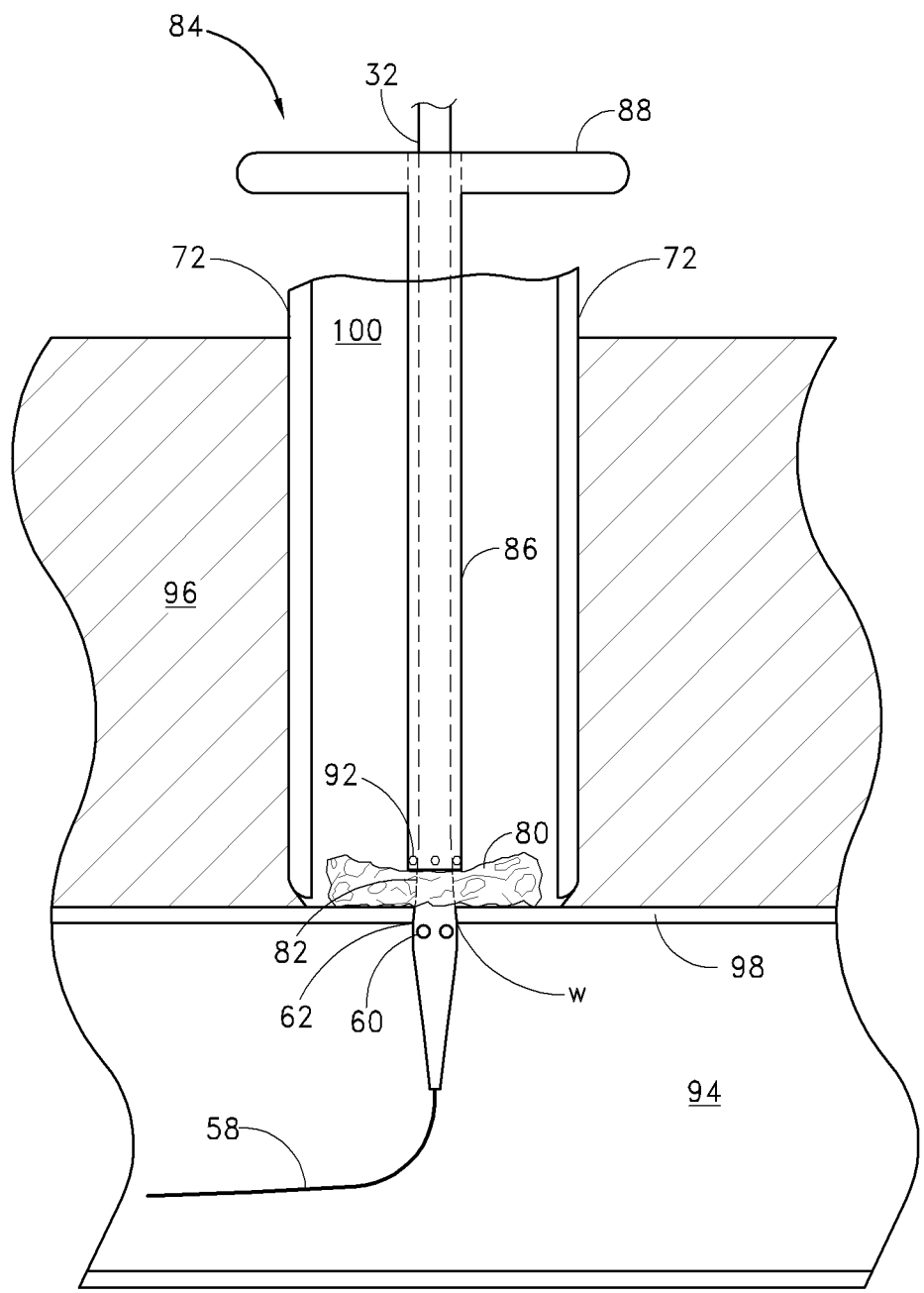
FIG. 6 shows the arrangement of FIG. 5, wherein a hemostatic sponge has been advanced into contact with the blood vessel wall.

With reference next to FIG. 6, once the puncture wound w has been precisely located, the push member 84 is advanced distally along the catheter 32, thus advancing the sponge 80 into contact with the vessel wall 98 so as to surround the puncture wound w. As mentioned above and discussed in more detail below, the sponge 80 comprises a hemostatic agent that will help accelerate blood clot formation at the wound site w in order to help the wound heal faster.

Preferably, the sponge 80 is at least partially coated with an adhesive so that the sponge will at least partially bond to the vessel wall 98. Alternatively, or in addition, flowable adhesive can be delivered into the field around the puncture wound before the sponge is advanced into contact with the vessel wall. Of course, the sponge can be delivered without using any adhesive.

Figure 7:
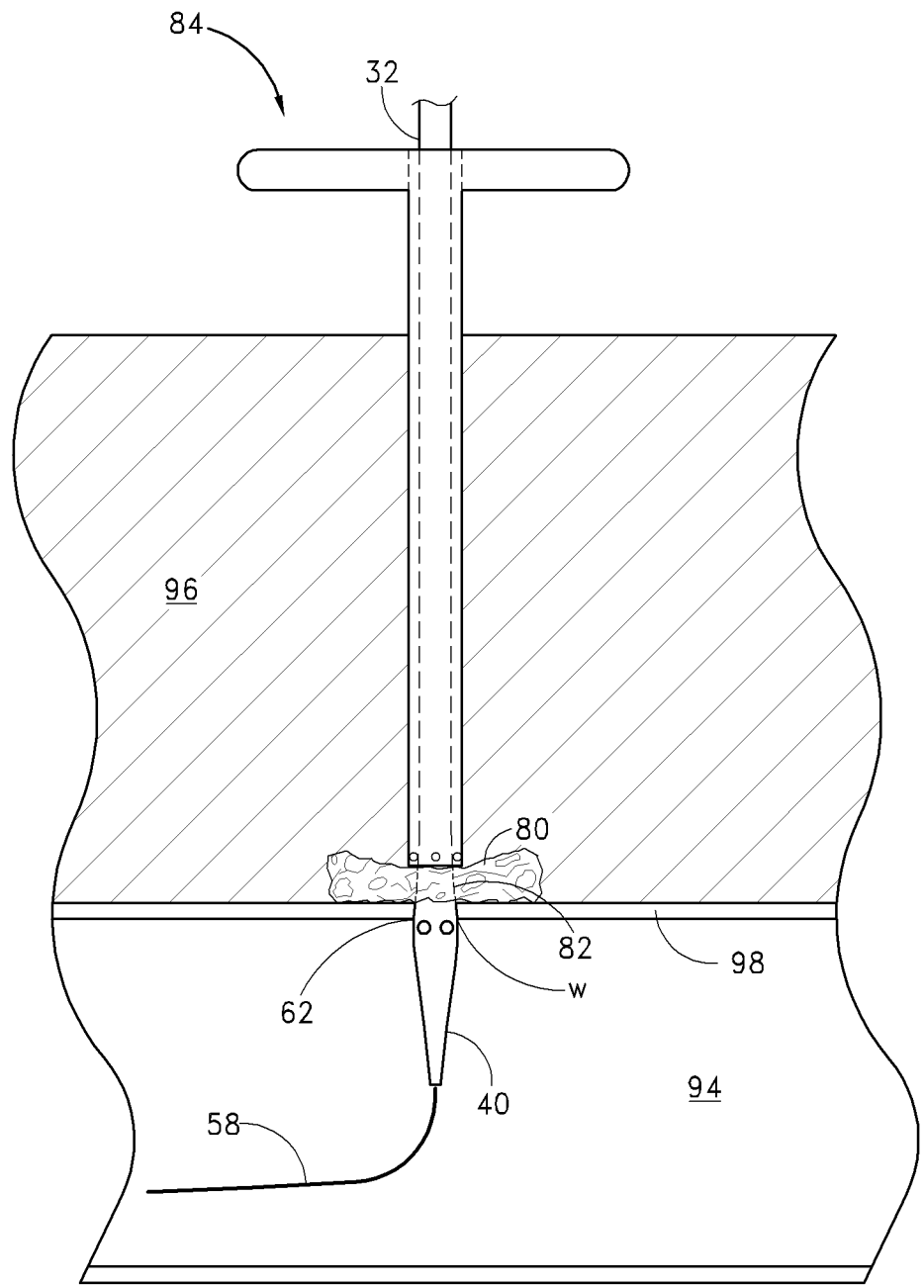
FIG. 7 shows the arrangement of FIG. 6, with the retractor arms removed.

The sponge 80 preferably is mounted onto the catheter 32 so as to substantially encircle the catheter 32. Thus, since the tip 40 of the catheter is disposed in the wound, the sponge 80 substantially surrounds the wound w when the sponge is positioned adjacent the vessel wall 98. When the sponge 80 is in place adjacent the wound w, the retractor 70 can be removed, as shown in FIG. 7. When the retractor 70 is removed, the surrounding body tissues 96 collapse around the sponge 80 and push member 84. The push member 84 holds the sponge 80 in position while body tissue 96 surrounds the sponge 80 and while the adhesive cures.

Figure 8:
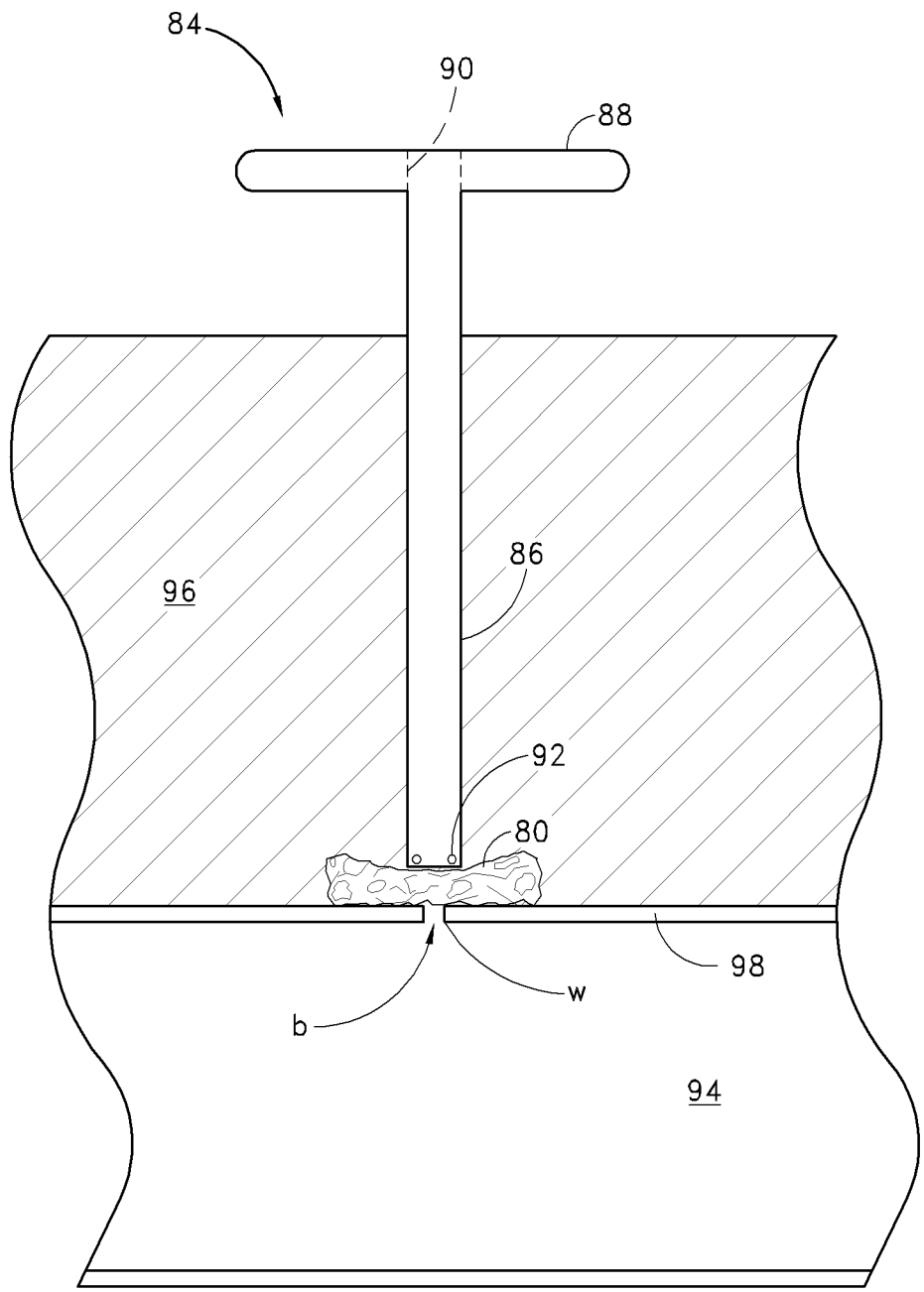
FIG. 8 shows the arrangement of FIG. 7 with the catheter and guidewire removed.

With reference next to FIG. 8, with the push member 84 in place, the catheter 32 and guidewire 58 can also be removed from the patient. The passage 82 through the sponge 80, which had been occupied by the catheter 32, collapses onto itself so that it is substantially closed. The vessel wound w is no longer plugged by the catheter 32, and it is anticipated that blood b from the vessel 94 will flow into the sponge 80, at least partially soaking the sponge 80. Although the retractor 70 is removed prior to the catheter 32 in the above-discussed embodiment, it is to be understood that, in another embodiment, the catheter may be removed prior to the retractor.

In still another embodiment, additional pressure can be applied to the push member 84 in order to at least partially block blood flow through the blood vessel 94. In this manner, the clinician can control how quickly blood will flow through the wound w and into the sponge 80. Of course, other methods and apparatus can be used to temporarily reduce or stop blood flow through the vessel.

In a preferred embodiment, the sponge 80 comprises a material made of, soaked in or otherwise treated with a hemostatic agent. The agent is specially adapted to aid blood clotting. Thus, blood that flows into the sponge encounters the agent and will quickly become clotted, causing natural sealing of the wound through blood clotting. Sponge-like hemostasis agents are available and can include products such as Gelfoam™, Oxycell™ and Avitene™. Another material that can be used as a sponge is chitosan. These and other appropriate sponges may be impregnated with agents such as thrombin, a liquid clotting agent, to help accelerate blood clot formation and Hemadex™, which is available from Medafor, Inc. Another material that may advantageously be used is a collagen Ultrafoam™ sponge marketed by C.R. Bard/Davol, Inc. The Ultrafoam™ sponge is made from Avitene™ collagen, a natural clotting agent, and does not require the addition of thrombin. This reduces preparation time and the risk that a patient will experience a potentially hazardous reaction to bovine thrombin. Other medicants can also be included in the sponge. For example, antibiotic medicines, anti-inflammatory drugs, healing aids, and the like can be impregnated into the sponge material.

In accordance with one preferred embodiment, the hemostatic material and/or sponge comprises a fibrous polysaccharide substrate, most preferably comprising chitosan. The substrate may be formed in various manners, as discussed in Applicant's copending applications, both of which are entitled "DEPLOYABLE HEMOSTATIC AGENT", which were filed on Aug. 22, 2004 as U.S. Provisional Application No. 60/479,096 and U.S. Provisional Application No. 60/479,097. The entirety of both of these applications is hereby incorporated by reference. In accordance with another preferred embodiment, the hemostatic sponge comprises a hydrophilic material that will preferentially bond with wet surfaces such as a blood vessel and surrounding tissue.

The sponge-like material preferably is soft and pliable and will conform to the structure of the blood vessel, the wound and the field around the blood vessel. Thus, the sponge-like material is specially suited for use in the confined space surrounding a vascular puncture. Additionally, the hemostatic sponge 80 will be held in place by the tissue 96 surrounding the puncture wound w, which tissue 96 collapses over the sponge 80 when tools such as the retractor 70 are removed.

Figure 9:
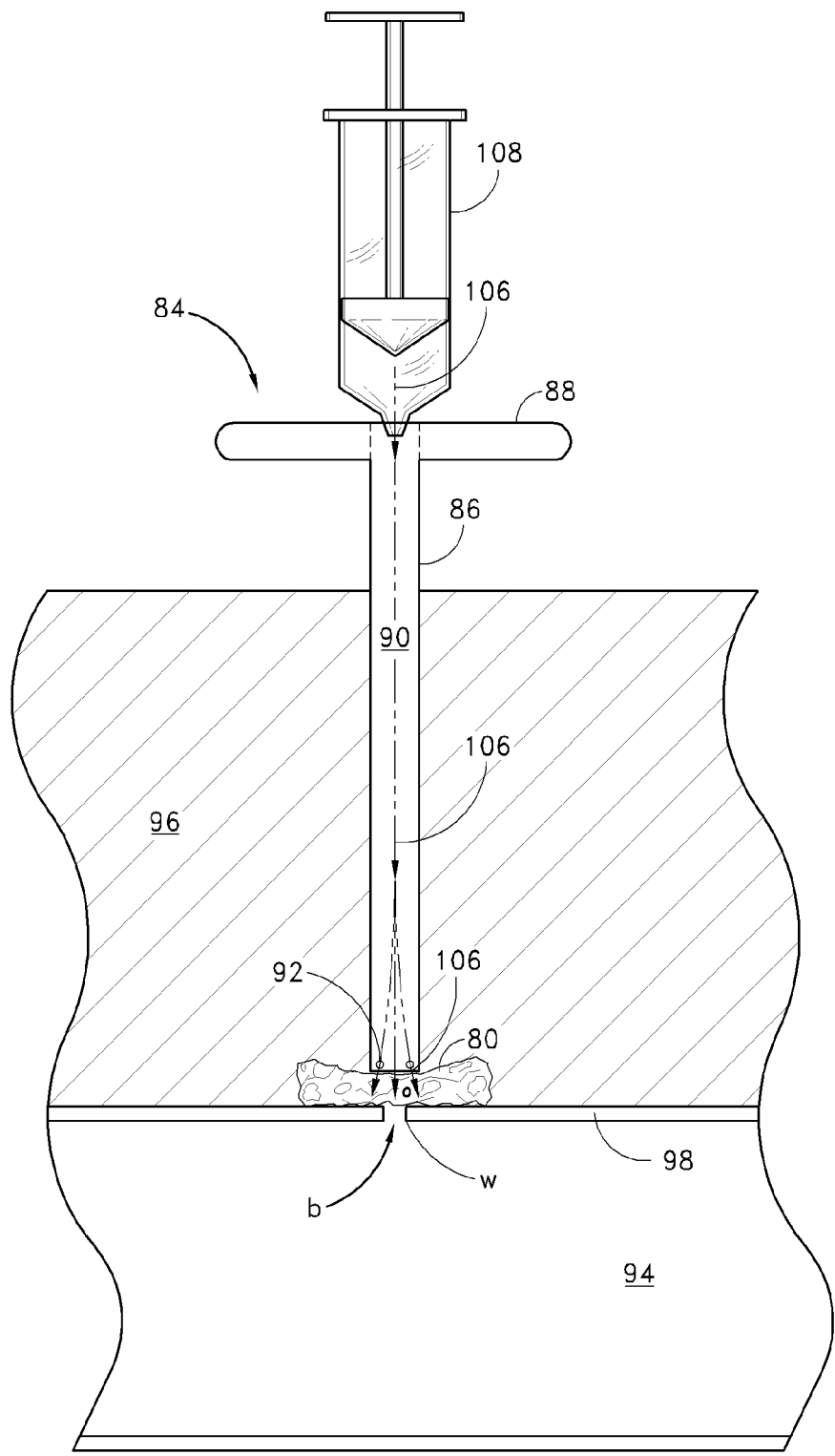
FIG. 9 shows the arrangement of FIG. 8, wherein a flowable adhesive is being delivered to the sponge.

To further help hold the sponge 80 in place, flowable adhesive 106 from a source of adhesive 108 can be delivered through the lumen 90 of the push member 84 and onto the sponge 80, as shown in FIG. 9. The adhesive 106 flows through the open distal end of the push member 84 and also through the holes 92 through the push member body portion 86. Upon curing, the adhesive 106 can form a sealing layer around and within the sponge 80, thus confining the blood b to the sponge area. This helps minimize bleeding and even further speeds clot formation. In one embodiment, adhesive, when cured, is substantially non-porous, and thus confines blood to a desired area. Adding adhesive 106 will also facilitate more complete closure of the passage through the sponge, which passage was vacated by the catheter 32. Further, the adhesive 106 will help hold the sponge 80 in place relative to the puncture wound w and the surrounding tissue 96.

As discussed above, prior to being advanced into contact with the blood vessel wall, the sponge 80 may be soaked in an adhesive or, more preferably, coated with a layer of adhesive. In this manner, adhesive distribution on the sponge can be controlled. By controllably applying a coating of adhesive around the outer surface of the sponge, the adhesive will bond the sponge to the area surrounding the blood vessel wound w, including the vessel 94 itself, and also can form a perimeter seal of the sponge when the adhesive cures. The coating of adhesive can act as a non-porous or selectively-porous membrane confining the blood b to the sponge 80. It is to be understood that a coating of adhesive may be used instead of or in addition to applying additional adhesive 106 through the push member 84.

Various kinds of flowable adhesives may be acceptable for use with the sponge. For example, fibrin tissue sealants such as Tisseel®, which is available from Baxter Healthcare Corp., may be appropriate. Other commercially available adhesives that may be appropriate include Bioglue™, available from Cryolife, Inc., and Floseal™, which is available from Fusion Medical Technologies. Various cyanoacrylate adhesives are currently commercially available and can be used with this invention. Of course, any product that is capable of sealing the sponge or at least retarding blood flow through or beyond the sponge would be acceptable. It is also to be understood that certain adhesives will not require that the field and/or the outer wall of the blood vessel be cleared before the adhesive is injected.

Curing time and ease of use will vary depending on the adhesive used. For example, some adhesives cure to a malleable gel-like state within a few seconds, while others will cure directly to a hardened state in a few minutes. The time period for curing is chosen to allow the clinician to advance the sponge into position adjacent the wound and in contact with the artery, at which time the sponge will begin to be bonded to the vessel wall and substantially sealed by the adhesive. It should be appreciated that any acceptable adhesive having any acceptable curing time may be used. In accordance with this description, an adhesive is considered to be cured when it is adhered to surrounding tissue, and when it does not spontaneously flow.

The push member 84 may be kept in place for any reasonable time period in order to allow the adhesive 106 to cure. Also, multiple sponges can be used, if desired. Preferably, however, the adhesive 106 will cure sufficiently in about five minutes or less. Other tools, such as an ultraviolet light source or a heat application device, may be used to help speed adhesive curing.

Figure 10:
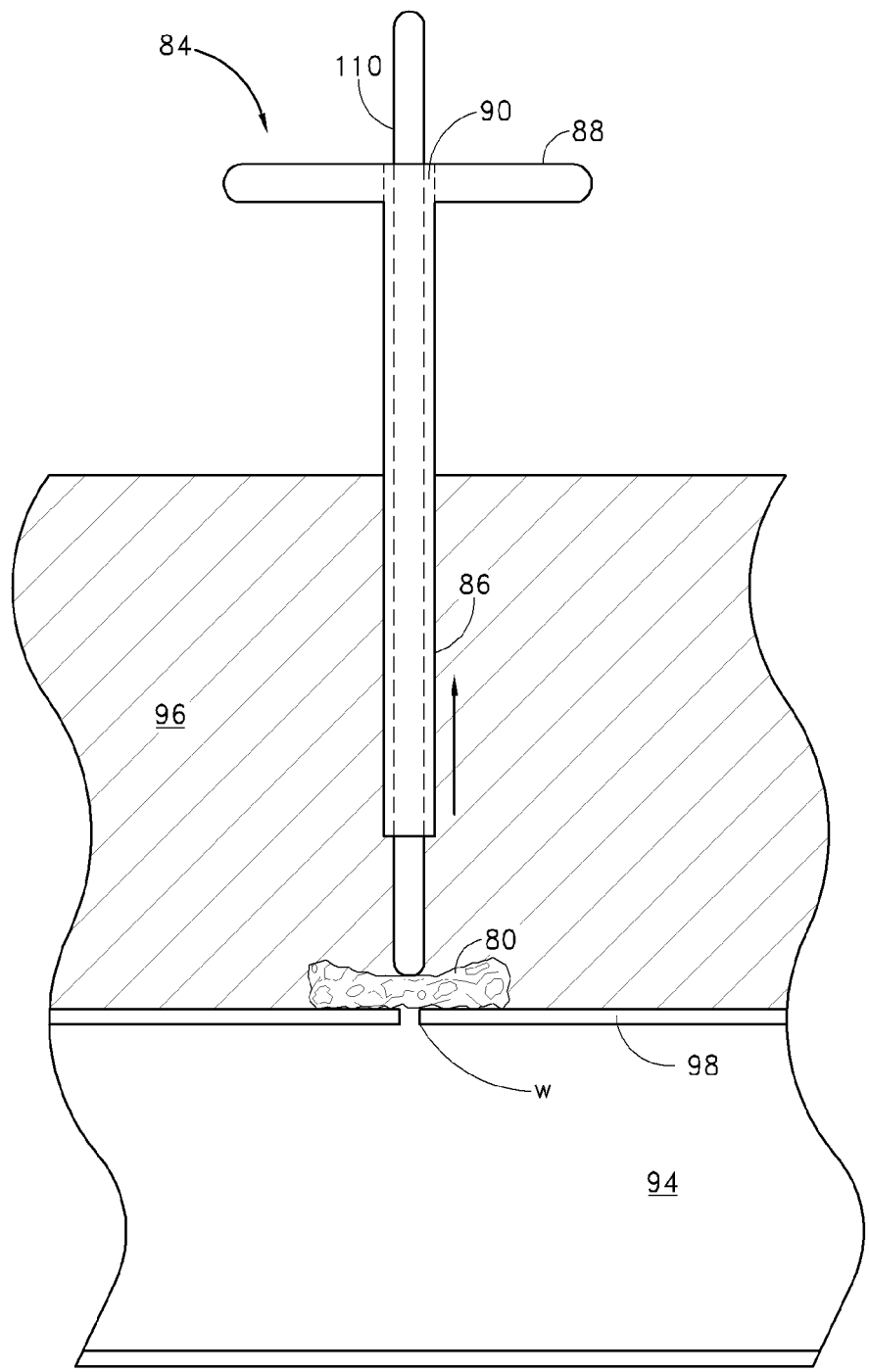
FIG. 10 shows the arrangement of FIG. 8, wherein the push member is being removed from the patient.
Figure 11:
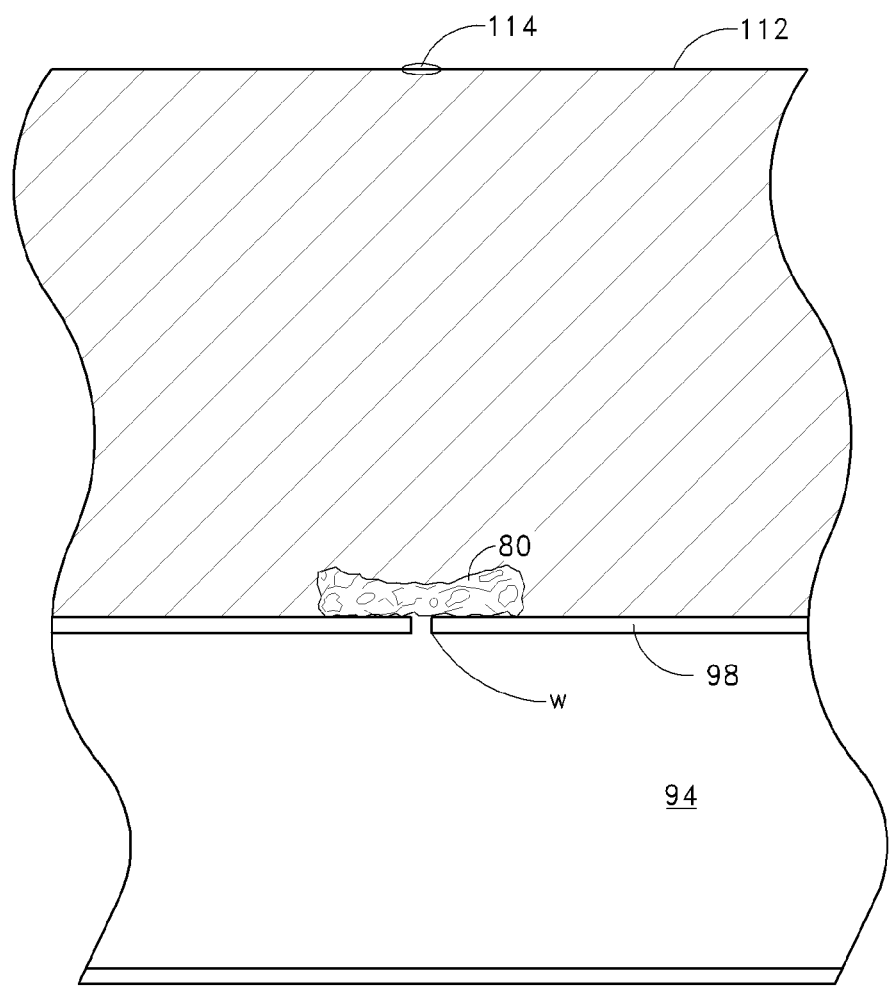
FIG. 11 shows a sealed puncture wound after treatment with an embodiment of the device and method.

Once the sponge 80 is correctly placed, the push member 84 can be removed. Removal of the push member 84 can be aided by a release rod 110 which, as shown in FIG. 10, is advanced through the push member lumen 90 and into contact with the sponge 80. The release rod 110 holds the sponge 80 in place as the push member 84 is withdrawn from the patient. Thus, the release rod 110 engages the sponge 80 so as to provide counter traction when the push member 84 is withdrawn. In this way, the push member 84 can be removed even if some adhesion occurs between the sponge 80 and the push member 84. With reference next to FIG. 11, once the release rod 110 is withdrawn, the patient's skin 112 is closed by any appropriate closure media such as, for example, sutures 114. The hemostatic sponge 80 is left in place. The body's natural blood clotting process will plug and repair the vascular wound w with the aid of the hemostatic sponge 80. Thus, healing will proceed without the danger of false aneurysms, missed or faulty wound closure, or the like.

As discussed above and shown in FIGS. 1 and 7, the hemostatic sponge 80 circumferentially surrounds the catheter 32, and the catheter 32 preferably extends through a puncture hole 82 through the sponge 80. When the catheter 32 is removed, however, the hole 82 remains. Sponges that are relatively elastic will spring back into place, filling the hole 82. However, some hemostatic sponge materials have relatively poor elastic resilience and mechanical strength. Such materials may not be able to spring back into place to fill the hole. This is problematic because the hole 82 is aligned with the blood vessel wound w; thus, blood b may flow substantially unimpeded through the hole 82, possibly leading to complications. Also, adhesive that is injected can possibly flow through the hole 82 in the sponge 80 and further through the wound w and into the bloodstream.

Figure 12:
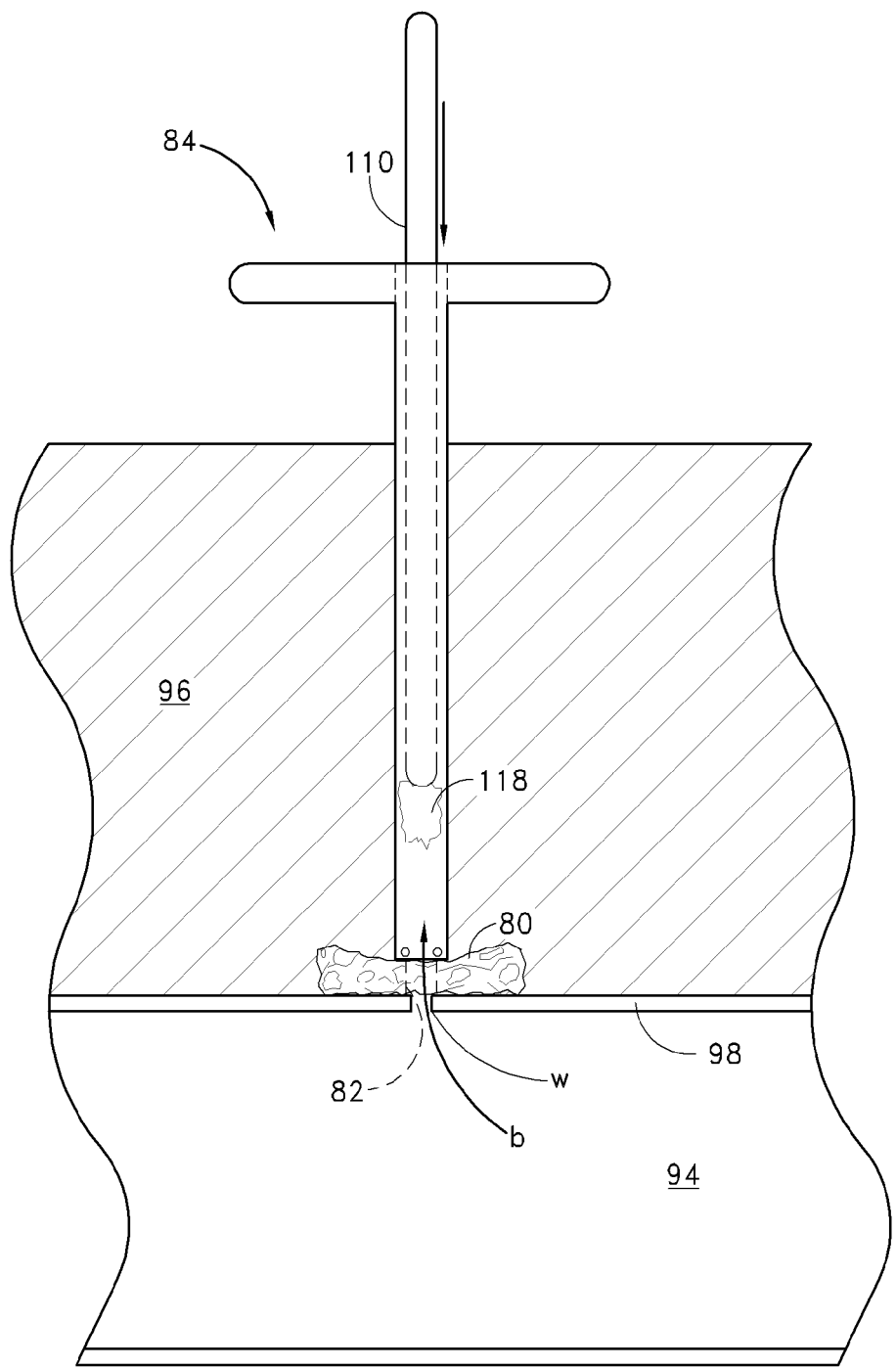
FIG. 12 shows an embodiment wherein an additional sponge is being advanced toward the wound.
Figure 13:
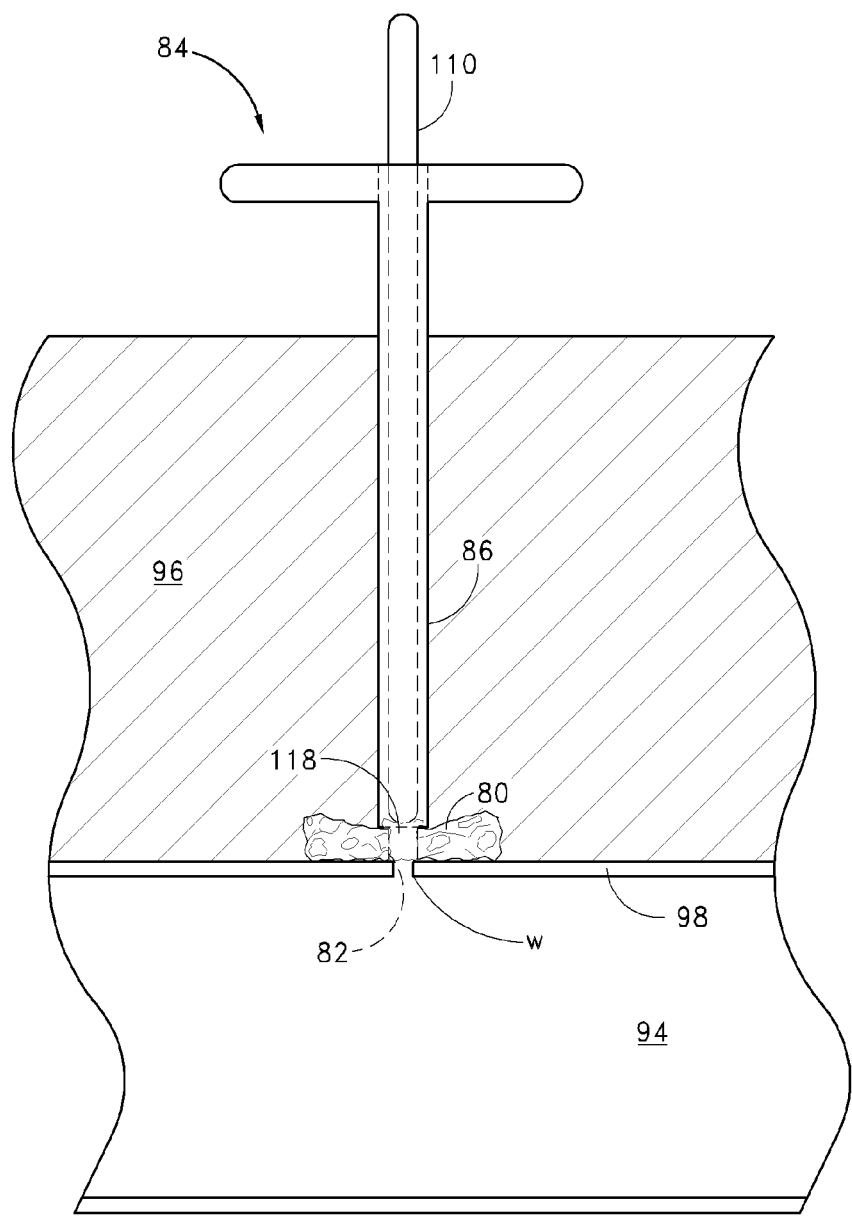
FIG. 13 shows the embodiment of FIG. 12 with the additional sponge in place.

Accordingly, in another embodiment depicted in FIGS. 12 and 13, the release rod 110 can be used to advance one or more additional hemostatic members 118 through the push member lumen 90 and into contact with the original sponge 80. The additional sponge material 118 can help further plug the hole 82 in the sponge 80 through which the catheter 32 was disposed, and will stem the flow of blood b with the hemostatic sponge material 118, which will facilitate blood clotting. The additional sponge material 118 will also plug the hole 82 left in the original sponge 80 so that adhesive that may be added later will be blocked from entering the wound w.

Figure 14:
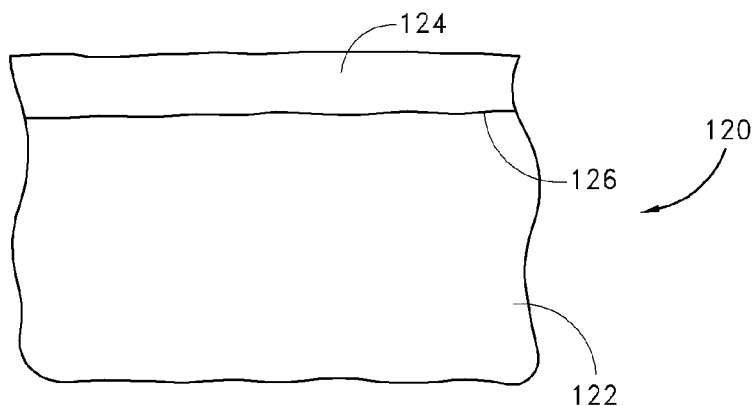
FIG. 14 shows another embodiment of a hemostatic sponge member.
Figure 15:
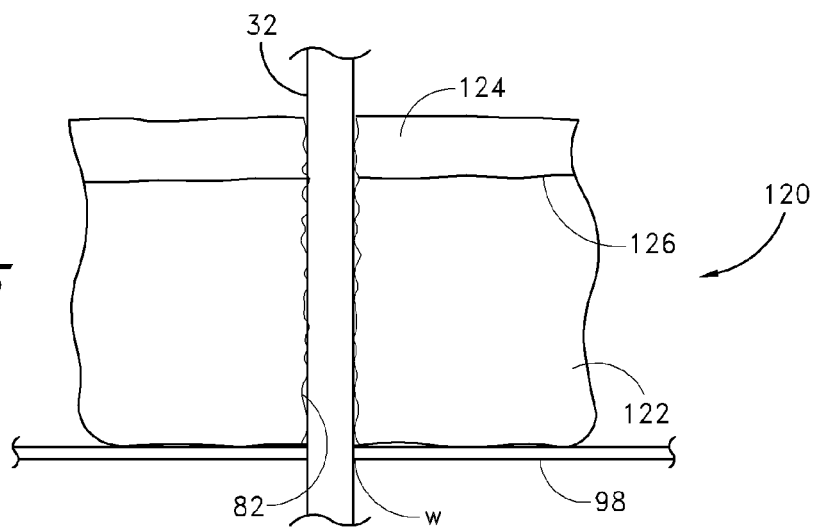
FIG. 15 shows the sponge member of FIG. 14 in contact with the vessel wall and having a catheter extending therethrough.
Figure 16:
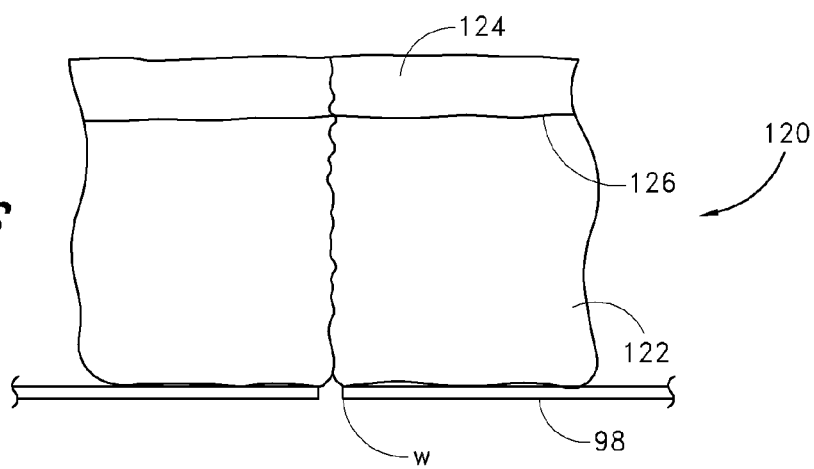
FIG. 16 shows the arrangement of FIG. 15 with the catheter removed.

With reference next to FIGS. 14-16, another embodiment of a hemostatic sponge member 120 comprises a hemostatic sponge layer 122 and a highly elastic layer 124. A layer of cement 126 attaches the hemostatic layer 122 to the elastic layer 124. Alternatively, the hemostatic layer 122 and elastic layer 124 can be integrally formed. As with the hemostatic sponge 80 described above, the hemostatic layer 122 comprises a hemostatic agent which facilitates and speeds blood clotting. The elastic layer 124 improves the overall elasticity and mechanical strength of the sponge 120. Preferably the elastic layer 124 comprises a polymer having relatively high elastic resilience and mechanical strength. Polymer elastomers such as polyurethane, SDS and silicone rubber can advantageously be used for the elastic layer 124. It is to be understood that the elastic layer 124 preferably is non-toxic. Also, it is not necessary for the elastic layer to include a hemostasis agent or any other medicament.

As discussed above, the catheter 32 preferably extends through a puncture hole 82 through the hemostatic sponge 120. With continued reference to FIG. 15, the elastic layer 124 is preferably oriented on a side of the sponge 120 away from the wound w, while the hemostatic sponge layer 122 is oriented so as to directly contact the blood vessel wall 98 and wound w. With specific reference to FIG. 16, when the catheter 32 is removed from the hemostatic sponge 120, the highly elastic layer 124 will immediately retract, substantially sealing the hole 82. Since the hemostatic sponge layer 122 is connected to the elastic layer 124, the sponge material 122 will also be retracted, closing the hole. Accordingly, not only will the hole be sealed, but the hemostatic material 122 will fill the hole 82 so as to be placed directly in the path of blood b coming from the vascular wound w. Accordingly, more thorough and speedier blood clotting is achieved.

In the embodiment illustrated in FIGS. 1-9, the catheter comprises a single-lumen catheter. In another embodiment (not shown), the elongate catheter has a first lumen comprising a tube that extends from the distal end opening to the proximal end opening and slidingly accommodates the guidewire therewithin. The outer wall of the catheter defines a second lumen that concentrically surrounds the first lumen. The holes through the outer wall of the catheter open into the second lumen. Additionally, an access lumen communicates with the second lumen. In this embodiment, the distal and proximal openings, which accommodate the guidewire, do not communicate with the second lumen, which lumen communicates with the source of suction through the access lumen. Accordingly, in this embodiment, there may be less of a chance that body fluids will be drawn into the catheter through the distal and proximal guidewire openings than in an embodiment employing a single lumen. However, the single-lumen catheter can be less expensive to manufacture and can be expected to have a smaller diameter than the dual-lumen catheter.

Figure 17:
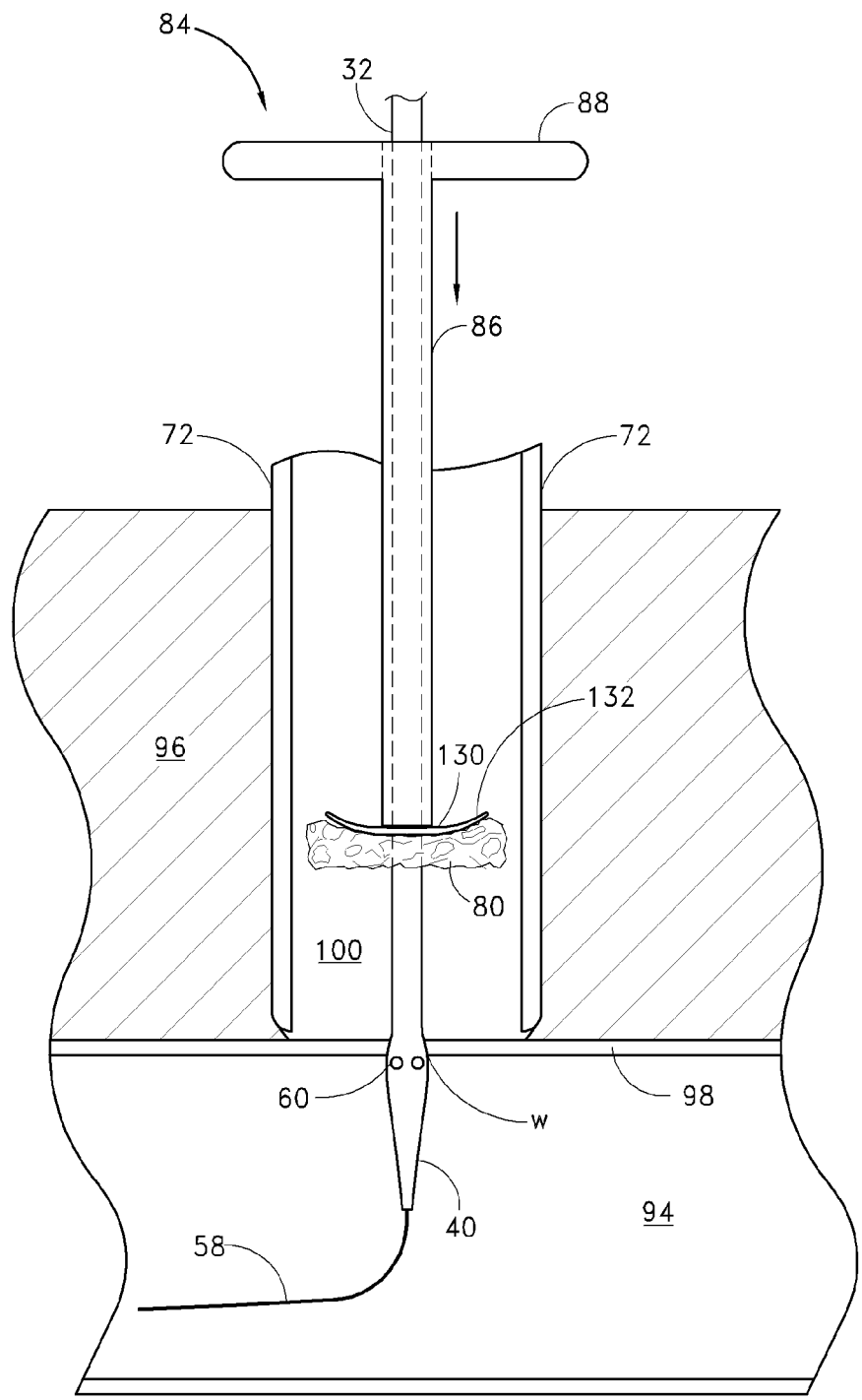
FIG. 17 shows an embodiment in which a lock member is provided proximal a hemostatic sponge member.
Figure 18:
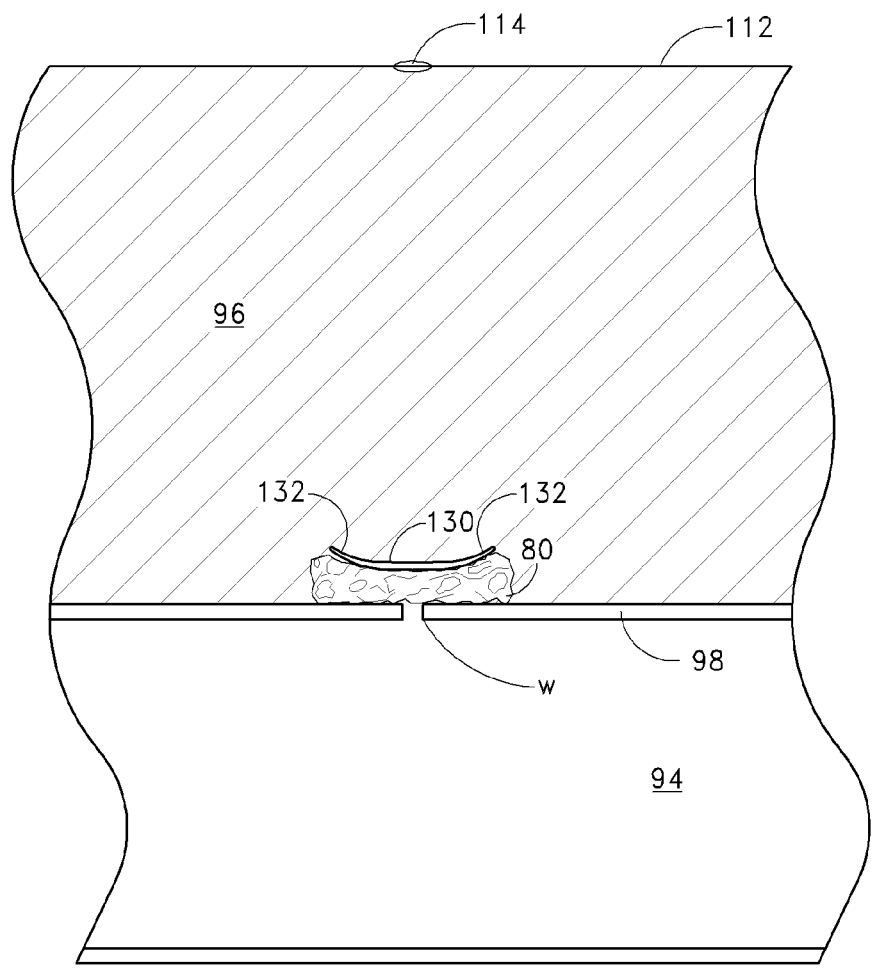
FIG. 18 shows a sealed puncture wound after treatment with the device of FIG. 12.

FIG. 17 shows another additional embodiment wherein a lock apparatus 130 is employed to help hold the sponge 80 in place against the artery wall 98. The lock apparatus 130 is preferably slidably disposed about the catheter 32 between the push member 84 and the sponge 80. The lock apparatus 130 accompanies the sponge 80 as it is advanced into position on the blood vessel wall 98 surrounding the vascular wound w. The lock apparatus 130 has arms that preferably are configured to allow movement through tissue 96 toward the wound w, but resist movement of the apparatus 130 in the direction away from the wound w. Thus, the lock apparatus 130 holds the sponge 80 tightly in place adjacent the wound as shown in FIG. 18.

It is to be understood that several forms of the lock apparatus may be advantageously employed. For example, in the illustrated embodiment, the lock apparatus 130 has swept-back arms 132 that are adapted so that the apparatus 130 can be advanced through a tissue 96 toward the vascular wound w, but cannot be moved away from the vascular wound w because the arms 132 will engage the surrounding tissue 96. In another embodiment, selectively actuable arms may be provided within the lock apparatus. A trigger may be provided so that the arms will extend into the surrounding tissue when the trigger is actuated, thus locking the device in place and holding the sponge next to the vascular wound.

The lock apparatus is preferably formed of a material that can be absorbed by the body over time. However, other materials, such as stainless steel, can be advantageously used.

Figure 19:
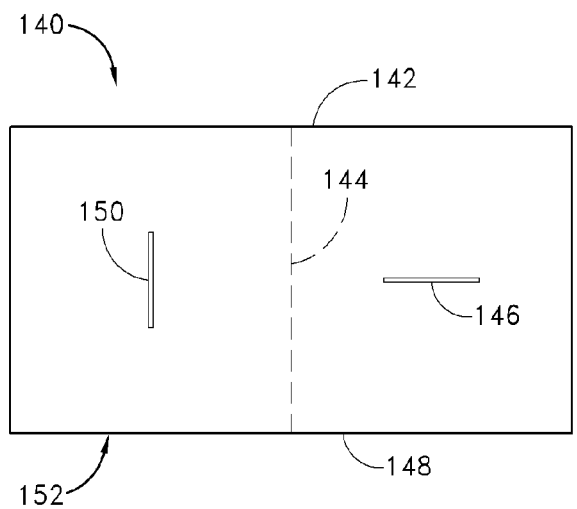
FIG. 19 shows a schematic view of an unfolded two-layer patch.
Figure 20:
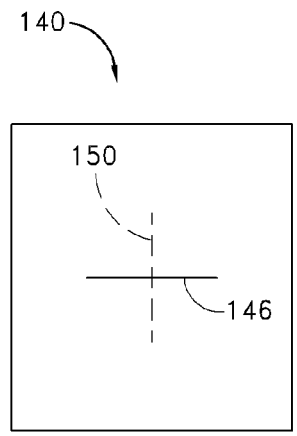
FIG. 20 shows the patch of FIG. 19 in a folded position.
Figure 21:
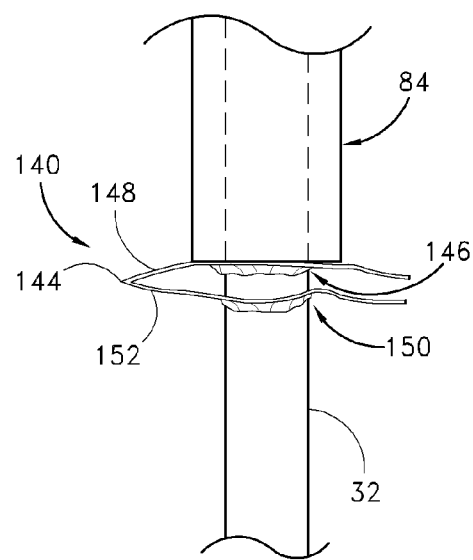
FIG. 21 shows the patch of FIG. 19 slidably mounted onto a catheter and being advanced by a push member.

In a further additional embodiment illustrated in FIGS. 19-21, a multi-layer patch 140 is used in addition to or instead of the sponge 80. The patch 140 may be soaked, coated or otherwise infused with a hemostatic agent and/or adhesive and is specially adapted to be advanceable over the catheter 32 and to cover the vascular wound w. As shown in FIG. 19, the patch 140 preferably comprises a single piece of material 142 having a fold line 144 disposed roughly down the middle thereof. A first slit 146 is provided in a first half 148 of the patch 140 and a second slit 150 is provided in a second half 152 of the patch 140. Preferably, the second slit 150 is substantially normal to the first slit 146. The patch material 142 is folded over itself as shown in FIG. 20 and is threaded over the catheter 32 as shown in FIG. 21. The catheter 32 fits through each of the slits 146, 150, which provide room for the catheter 32 to slidingly fit therethrough. However, as the patch 140 is advanced into position and the catheter 32 is removed from the patch, the slits 146, 150 overlap each other, leaving only a small hole, if any. Adhesive can be applied over the small hole and/or between the halves to ensure sealing of the patch and closure of the wound.

With reference next to FIGS. 22-26, another embodiment of a vascular wound closure apparatus is presented. The apparatus includes a retractor 200 and an elongate catheter 250.

Figure 23:
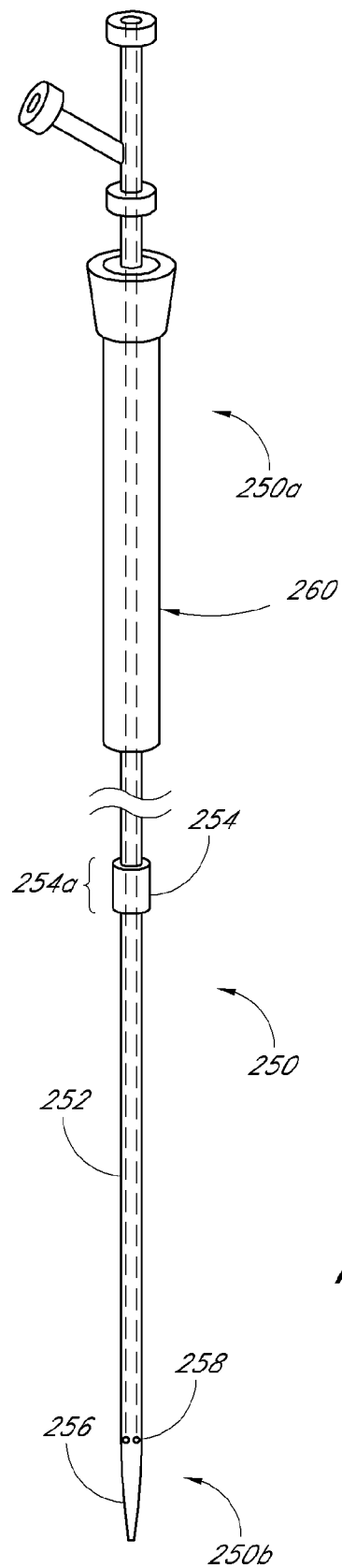
FIG. 23 shows a side view of a catheter for use according to the embodiment illustrated in FIG. 22.

With particular reference to FIG. 23, the catheter 250 has a proximal end 250a and a distal end 250b. A distal opening is formed through the distal end of the catheter and opens along a longitudinal axis of the catheter. A lumen 250c is defined within the catheter. A tip 256 at the distal end 250b of the catheter 250 preferably is tapered. A connector portion is provided on the proximal end 250a, which connector portion preferably includes a main lumen and a secondary lumen. The main lumen extends along the longitudinal axis of the catheter and is coextensive with the catheter lumen 250c. At least one indicator hole 258 is formed through a side wall of the catheter near the distal end. Preferably the catheter 250 is generally straight and is sized between about 4-8F and more preferably about 6F.

An outer surface 252 of the catheter 250 preferably has a generally cylindrical shape and includes a raised portion 254. In one preferred embodiment, the raised portion 254 defines a connection between two separate sections (not shown) of the catheter 250. In the illustrated embodiment, the raised portion 254 is cylindrical and includes a length 254a.

With continued reference to FIG. 23 a pusher member 260 preferably is movably disposed about the outer surface 252 of the catheter. The pusher member 260 preferably is configured to slide over the catheter 250. The pusher member 260 preferably has an inner lumen having a diameter greater than the raised portion 254 of the catheter 250 so that the pusher member 260 can slide over the raised portion 254.

Figure 22:
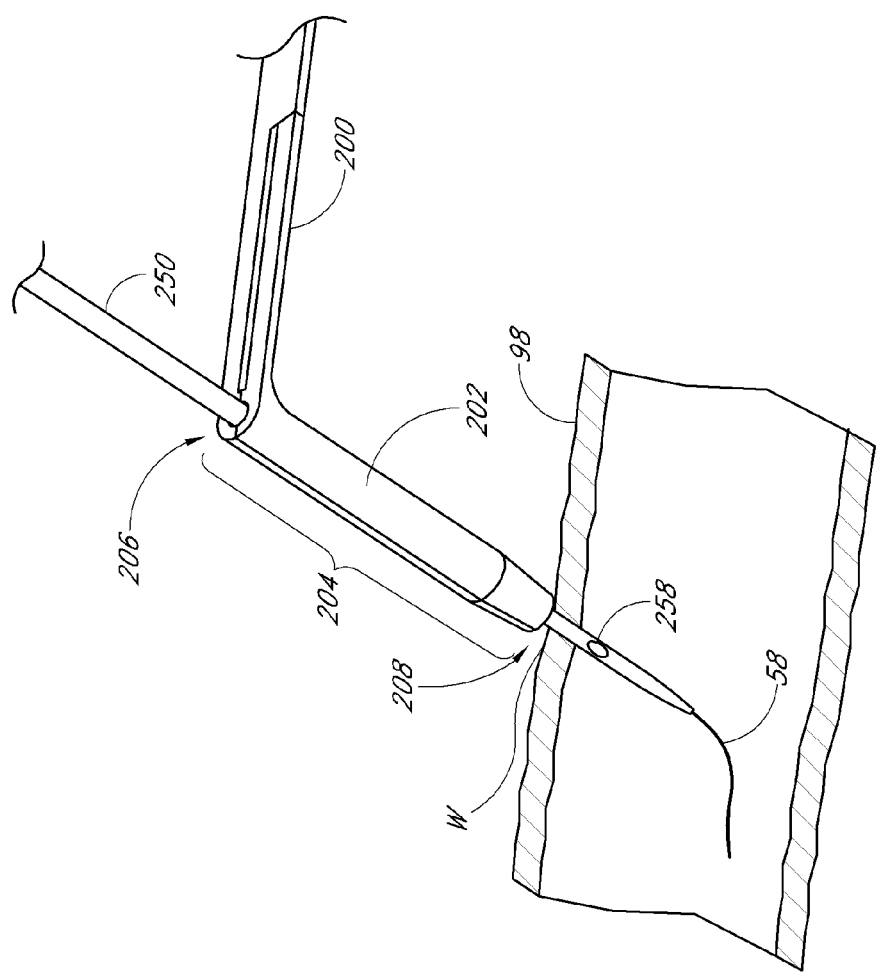
FIG. 22 shows another embodiment of a vascular wound closure apparatus.
Figure 24:
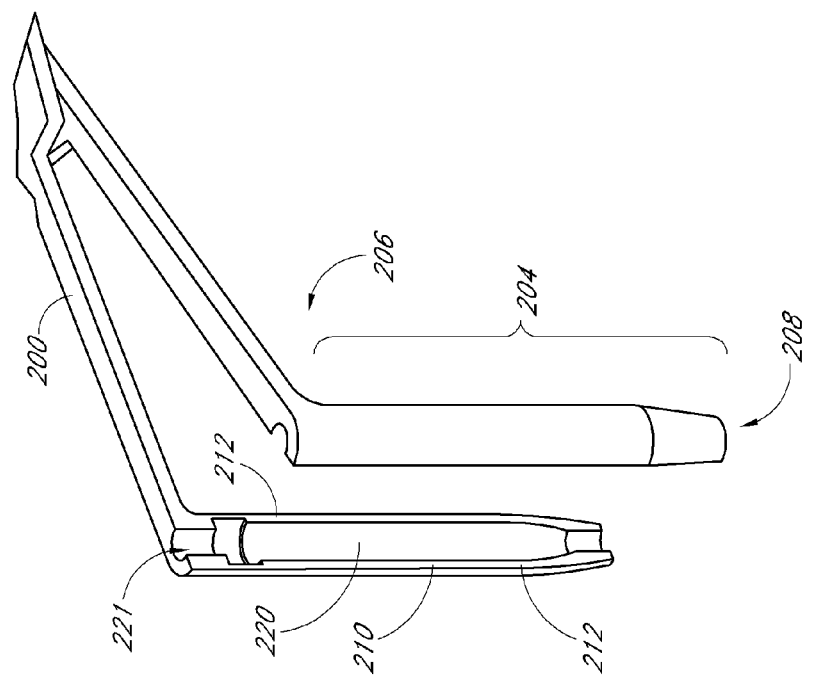
FIG. 24 shows a retractor portion of the apparatus of FIG. 22 with the retractor arms in an open position.
Figure 26:
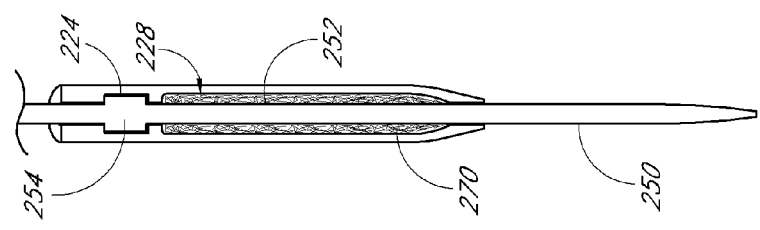
FIG. 26 shows the catheter of FIG. 23 disposed in the retractor arm of FIG. 25.
Figure 25:
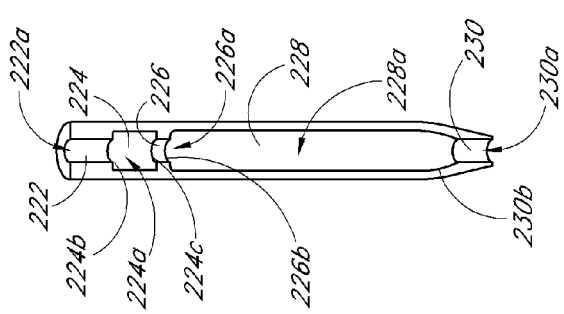
FIG. 25 shows a side plan view of one of the retractor arms illustrated in FIG. 24.

With reference next to FIGS. 24-26, the retractor 200 preferably is configured to be mounted onto the catheter 250. In the illustrated embodiment, the retractor 200 preferably has two retractor arms 202 movably connected to each other, each having a length 204 from a proximal end 206 to a distal end 208. The retractor arms 202 preferably are capable of being moved between an open position (see FIG. 24) and a closed position (see FIG. 22). When in the closed position, as illustrated in FIG. 22, the retractor arms 202 preferably enclose at least a portion of the catheter 250. Although the illustrated embodiment of the retractor 200 shows only two retractor arms 202, it should be understood that the retractor 200 can have more than two retractor arms 202.

With continued reference to FIGS. 24 and 25, each of the retractor arms 202 preferably defines an inner surface 210 generally facing the inner surface 210 of the other arm 202. Each inner surface 210 defines edges 212 that preferably extend along the length 204 of the arms 202. The inner surface 210 also preferably defines a cavity or channel 220 extending between the edges 212. The channel 220 preferably extends the length of the retractor arms 202. When the retractor arms 202 are in the closed position, as shown in FIG. 22, the channels 220 on the retractor arms 202 preferably combine to define a canal 221 extending the length 204 of the arms 202.

With reference to FIGS. 24-25, the channel 220 preferably comprises a proximal portion 222 disposed at the proximal end 206 of the retractor arms 202. In a preferred embodiment, the proximal portion 222 has a generally curved shape configured to removably receive and substantially contact and hold at least a portion of the catheter 250 in a fixed position when the retractor arms 202 are in the closed position. The proximal portion 222 also has a depth 222a generally orthogonal to the length 204 of the retractor arms 202. For example, the proximal portion 222 can have a semi-circular cross-section with a radius 222a about the same as that of an outer surface 252 of the catheter 250. However, the proximal portion 222 can have any shape configured to substantially contact the catheter 250 when the retractor arms 202 are in the closed position. Most preferably, the proximal portion 222 is sized and configured generally complementary to the catheter 250 so that the retractor 200 holds the catheter 250 generally snugly at the proximal portion 222.

With continued reference to FIGS. 25 and 26, the channel 220 preferably comprises a receiver portion 224 adjacent the proximal portion 222. The receiver portion 224 preferably has a generally curved shape and has a depth 224a generally orthogonal to the length 204 of the arms 202 that is greater than the depth 222a of the proximal portion 222. Accordingly, the receiver portion 224 defines an edge 224b between the receiver portion 224 and the proximal portion 222. The illustrated receiver portion 224 has a semi-circular cross-section with a radius 224a that is greater than the radius 222a of the proximal portion 222. Most preferably, the receiver portion 224 is generally complementary to the catheter raised portion 254 so as to receive the raised portion 254 therein.

The channel 220 also preferably comprises a contact portion 226 adjacent the receiver portion 224. Similar to the proximal portion 222, the contact portion 226 preferably is generally complementary to the catheter outer surface 252 and is configured to removably receive, and to substantially contact and hold the catheter 250 when the retractor arms 202 are in the closed position. The contact portion 226 preferably has a depth 226a generally orthogonal to the length 204 of the retractor arms 202. In one preferred embodiment, the depth 216a is similar to the depth 222a of the proximal portion 222. For example, the contact portion 226 can have a semi-circular cross-section with a radius 226a about the same as the radius 222a of the proximal portion 222. The depth 226a of the contact portion 226 is also preferably smaller than the depth 224a of the receiver portion 224, so that the receiver portion 224 defines an edge 224c between the receiver portion 224 and the contact portion 226.

With reference still to FIGS. 25 and 26, in the illustrated embodiment, the proximal portion 222 and contact portion 226 each are smaller than the receiver portion 224. Most preferably, the proximal portion 222 and contact portion 226 are configured so that the catheter raised portion 254 cannot slide through either portion 222, 226. Thus, when the raised portion 254 is disposed in the receiver portion 224 as shown in FIG. 26, the raised portion is constrained from moving proximally or distally. As such, the entire catheter 250 is longitudinally locked in place relative to the retractor 200 when the retractor arms 202 are closed about the catheter as shown in the FIG. 22.

The channel 220 further preferably comprises a compartment portion or chamber 228 adjacent the contact portion 226. The chamber 228 preferably has a generally curved shape and a depth 228a generally orthogonal to the length 204 of the retractor arms 202 greater than the depth 226a of the contact portion 226. For example, the chamber 228 can have a semi-circular cross-section with a radius 228a greater than the radius 226a. Further, the contact portion 226 defines an edge 226b between the contact portion 226 and the chamber 228. The chamber 228 is configured to receive a portion of the catheter 250 therein and to define a space 228b between the catheter 250 and the retractor arms 202. When the retractor arms 202 are in the closed position, the space 228b extends generally about the entire circumference of the catheter 250. The space 228b is configured to receive and accommodate a hemostatic material 270 therein so that it surrounds at least a portion of the outer surface 252 of the catheter 250. The hemostatic material 270 is further described below.

A distal portion 230 of the channel is defined adjacent the chamber 228 and has a depth 230a generally orthogonal to the length 204 of the retractor arms 202 smaller than the depth 228a of the chamber 228. The distal portion 230 preferably is generally complementary to the catheter outer surface 252 so as to substantially contact and hold the catheter 250 when the retractor arms 202 are in the closed position. For example, the distal portion 230 can have a semi-circular cross-section with a radius 230a. In one preferred embodiment, the radius 230a is about the same as the radius 226a of the contact portion 226 and/or the radius 222a of the proximal portion 222. A generally smooth transition section 230b preferably connects the chamber portion 228 and the distal portion 230.

With reference again to FIGS. 22-26, in practice, the hemostatic material 270 is preferably disposed about the outer surface 252 of the catheter 250 at a location between the raised portion 254 and the catheter holes 258. The catheter 250 is placed in the channel 220, while the arms 202 are in the open position, so that the raised portion 254 is disposed in the receiver portion 224 and the hemostatic material 270 is housed in the chamber 228. Preferably, the catheter 250 and retractor 200 are configured so that, when assembled, the distance between the distal end 208 of the retractor arms 202 and the indicator holes 258 is at least the same as the width of an artery wall. Preferably, said distance is at least about 0.5 to 2 millimeters.

When the retractor arms 202 are moved into the closed position with the raised portion 254 disposed in the receiver portion 224, the catheter 250 is longitudinally locked relative to the retractor 200. Thus, the catheter 250 and retractor 200 will move together even if longitudinal forces are exerted upon one or the other structure. In use, the apparatus is advanced into the patient so that the catheter 250 is advanced into the wound "w" as discussed above in connection with the embodiment discussed in connection with FIGS. 1-4. When blood "b" is observed in a viewing port (not shown) connected to the catheter 250, the retractor arms 202 are then preferably moved into the open position. The pusher member 260 is then advanced toward the distal end 250b of the catheter 250 to engage and advance the hemostatic material 270 into contact with the wound w.

In a preferred embodiment, the hemostatic material 270 comprises Hemadex™, which is available from Medafor, Inc. of Minneapolis, Minn. In other embodiments, the hemostatic material 270 can be infused with any number of medications associated with the treatment of wounds. Additionally, the hemostatic material 270 can have a variety of structures. For example, in one preferred embodiment, the hemostatic material 270 has a tightly cohesive form. In another preferred embodiment, the hemostatic material 270 has a generally loose and puffy form similar to that of a cotton puff or ball.

With reference next to FIGS. 27-33, another embodiment of a vascular wound closure assembly 300 comprises a catheter 310 having a proximal end 312 and a distal end 314, and defining a lumen (not shown) therebetween. A pusher member 330 having a proximal end 332 and a distal end 334 is slidably disposed on the catheter 310. A delivery tube 350 having a proximal end 352 and a distal end 354 is slidably disposed on the catheter 310 and is positioned distal of the pusher member 330. The closure assembly 300 preferably is made of a polymeric material, such as polypropylene. Preferably, the assembly 300 is also made of hypoallergenic materials.

Figure 28:
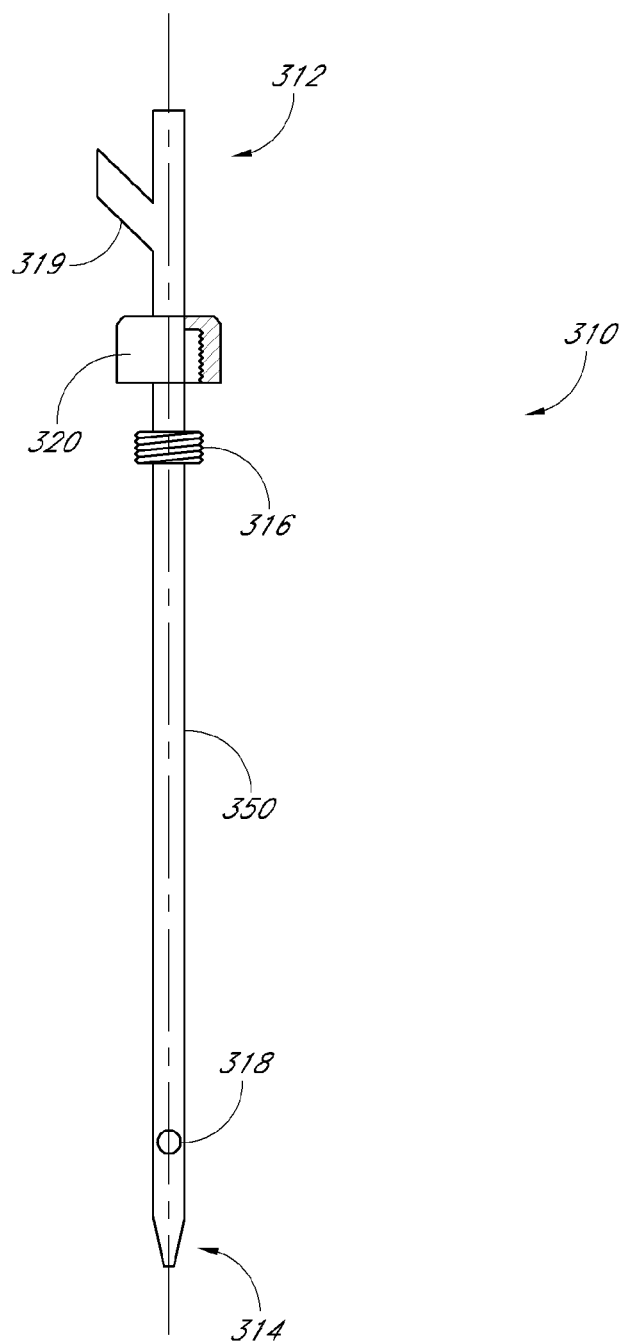
FIG. 28 shows a side view of a catheter according to the embodiment illustrated in FIG. 27.

With particular reference to FIG. 28, the catheter 310 preferably comprises a stop member 316 disposed in a fixed position about the catheter surface 310a. The distal end 314 preferably is tapered, and catheter holes 318 are formed through a side of the catheter 310 proximal of the distal end 314. In one embodiment, the catheter 310 preferably comprises a secondary branch 319 disposed at the proximal end 312, and having a secondary lumen (not shown) connected to the lumen of the catheter 310. The secondary branch 319 preferably is configured to operatively connect to a variety of devices used in the closure of vascular wounds, such as a suction device. For example, in one embodiment, a syringe can be connected to the secondary branch 319 to pull a vacuum through the catheter 310.

A coupling member 320 preferably is movably disposed about the catheter 310 and is configured to mechanically couple to the stop member 316. In the illustrated embodiment, the stop member 316 is threaded on its outer surface and the coupling member 320 is threaded on its inner surface so that the respective threads are engagable so that the coupling member 320 and catheter 310, when engaged, do not move longitudinally relative to one another. As such, the member 320 and catheter 310 are releasably coupled to one another. In other embodiments, other suitable mechanical coupling mechanisms can be used. For example, a detent and catch mechanism or a j-lock mechanism can also be acceptably employed.

In this description, the term releasably coupled is a broad term used in its ordinary sense and referring to, without limitation, to members being attached or affixed to one another in a manner so that they can be decoupled from one another. For example, without limitation, members can be coupled with threads, a detent mechanism, a coformed yet breakable bridge, such as flashing from injection-molding, an adhesive, or the like.

Figure 29:
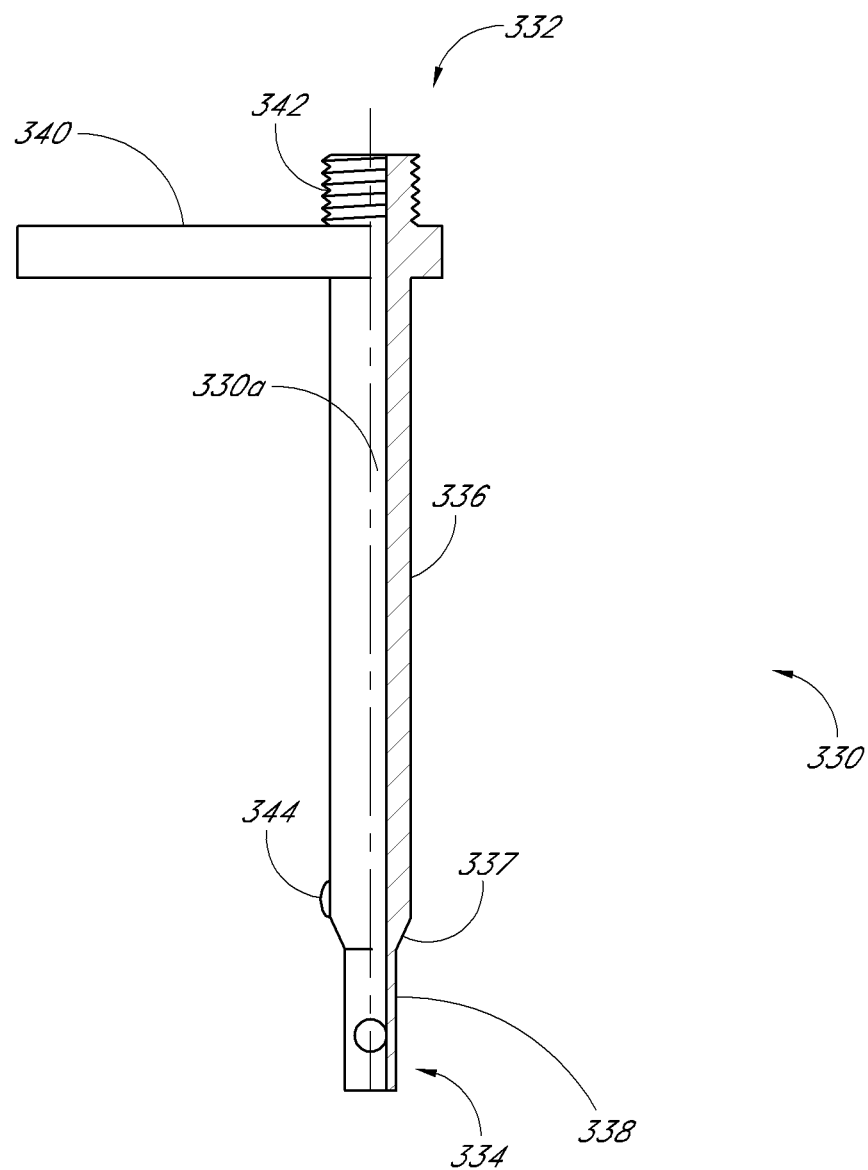
FIG. 29 shows a partially cutaway view of a pusher member according to the embodiment illustrated in FIG. 27.

With particular reference next to FIG. 29, the pusher member 330 preferably comprises a generally cylindrical central portion 336, a generally conical transition portion 337 and a generally cylindrical distal portion 338. The diameter of the central portion 336 preferably is larger than the diameter of the distal portion 338. The pusher member 330 preferably defines a canal 330*a* that extends from the proximal end 332 to the distal end 334 and which is preferably configured to slidably receive the catheter 310 therethrough. For example, the canal 330*a* can have a circular cross-section with a diameter larger than the diameter of the catheter surface 310*a*. However, the canal 330*a* is not large enough to fit over the catheter stop member 316. As such, the pusher member 330 cannot be moved proximally over the catheter 310 beyond the stop member 316.

The pusher member 330 preferably comprises a handle 340 near the proximal end 332. It is to be understood that the pusher member 330 can comprise more than one handle 340.

Figure 27:
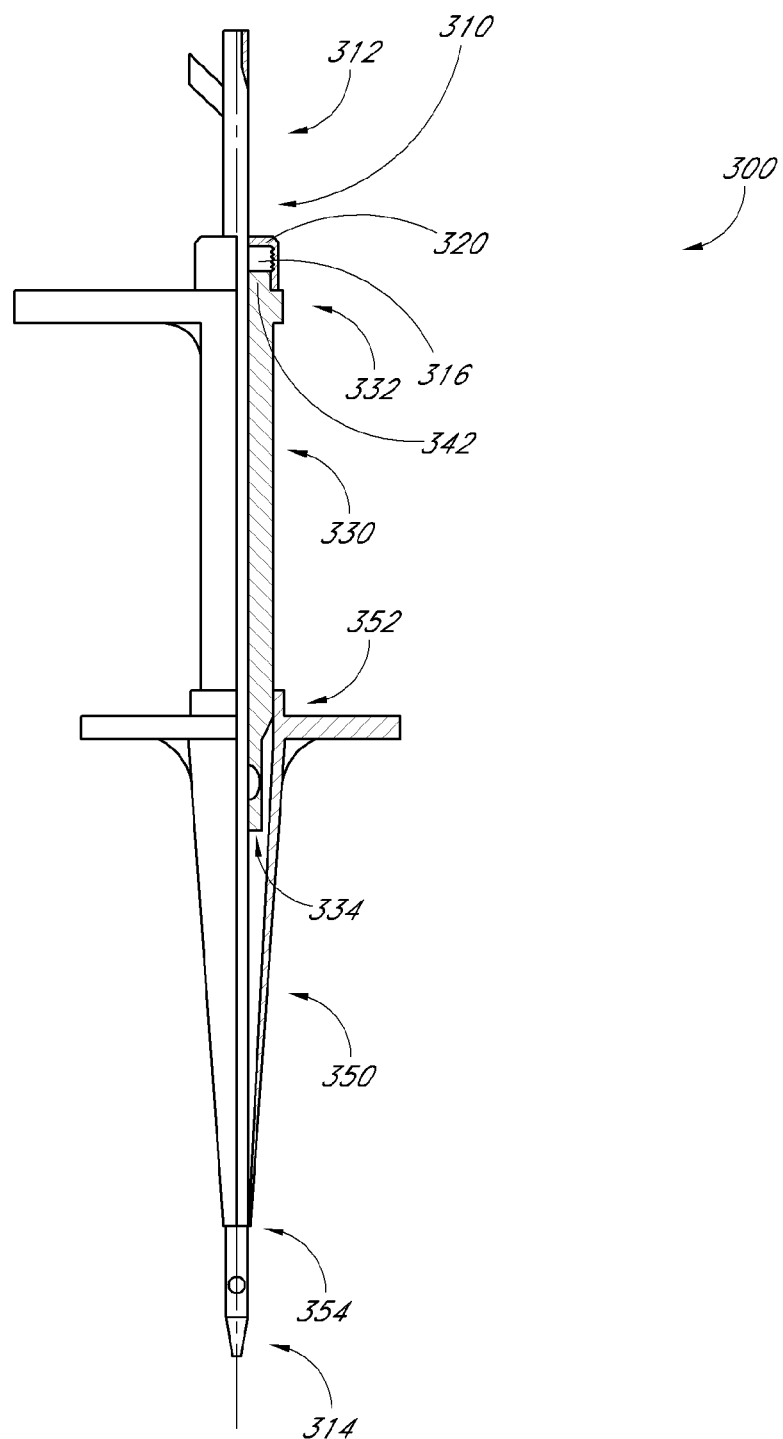
FIG. 27 shows a partially cutaway view of another embodiment of a vascular wound closure apparatus.

A proximal coupling member 342 is disposed at the proximal end 332. In the illustrated embodiment, the proximal coupling member 342 comprises threads on its outer surface sized and configured to engage the threads of the coupling member 320. As shown in FIG. 27, the catheter coupling member 320 is configured to engage both the stop member 316 and the pusher member proximal coupling member 342 so as to selectively hold the pusher 330 longitudinally fixed relative to the catheter 310.

A distal coupling member 344 is disposed proximal the transition portion 337. In the illustrated embodiment, the distal coupling member 344 comprises a generally hemispherical raised portion.

Figure 30:
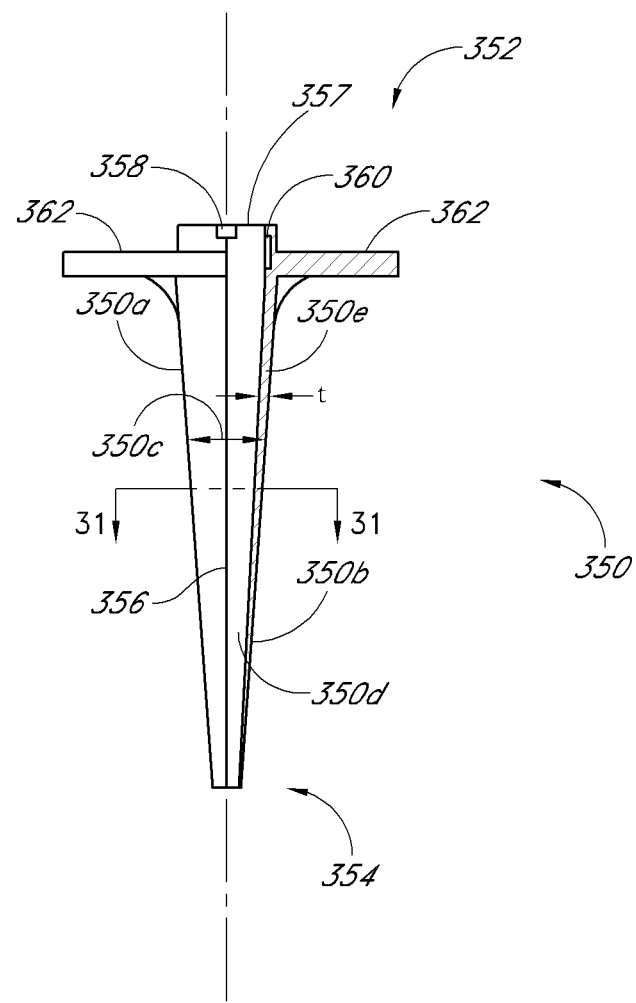
FIG. 30 shows a partially cutaway view of a delivery tube according to the embodiment illustrated in FIG. 27.

With particular reference next to FIGS. 30-31, the delivery tube 350 preferably has a body 350*a* with a conical outer surface 350*b* having a generally decreasing diameter 350*c* between a top edge 357 at the proximal end 352 and the distal end 354. A wall 350*e* of the delivery tube 350 has a thickness "t". The delivery tube wall 350*e* preferably defines a chamber 350*d* extending from the proximal end 352 to the distal end 354. The chamber 350*d* preferably is conical in shape, and preferably is configured to receive hemostatic material 270 therein between the catheter and the wall. The proximal end 352 of the delivery tube 350 also is preferably configured to receive at least a distal portion of the pusher member 330. The distal end 354 of the delivery tube 350 has a distal opening that is configured to receive the catheter 310 extending therethrough.

With particular reference to FIG. 31, the delivery tube 350 preferably comprises weakened portions 356. In the illustrated embodiment, the weakened portions 356 comprise portions of the tube 350 having a reduced thickness "t". The reduced thickness weakened portions 356 preferably extend from at or near the proximal end 352 to the distal end 354 of the delivery tube 350. The weakened portions 356 define a preferential breaking or deformation zone of the delivery tube 350 so that when a force beyond a specified threshold is applied, the tube will deform or break in the vicinity of the weakened portions 356. In the illustrated embodiment, the delivery tube 350 has two weakened portions 356 comprising elongate sections of reduced thickness "t" diametrically opposed to each other. Preferably, the elongate weakened portions 356 extend the entire length of the delivery tube 350.

In accordance with this description, the term weakened portion is a broad term used in its ordinary sense and referring to, without limitation, a zone or area that preferentially breaks, bends, stretches, expands or otherwise deforms upon application of a threshold force. In the illustrated embodiment, the weakened portions comprise portions that are relatively thin. In accordance with other embodiments, a weakened portion can include, without limitation, a portion of material that is scored, perforated, physically or chemically treated, or the like. Further, a weakened portion can comprise an elastic or easily deformable material that may or may not be a different material than the rest of the member.

In the illustrated embodiment, as shown in FIG. 31, the delivery tube 350 has two weakened portions 356. However, it is to be understood that the delivery tube 356 can have one or a plurality of weakened portions 356.

In one embodiment, the delivery tube 350 preferably comprises separation starter portions 358 disposed at the proximal end 352. The starter portions 358 are preferably disposed adjacent and aligned with the weakened portions 356. In the illustrated embodiment, the starter portions 358 are notches 358 aligned with the weakened portions 356. In other embodiments starter portions 358 can be provided having other shapes.

The delivery tube 350 further comprises a coupling portion 360 disposed at the proximal end 352. The coupling portion 360 preferably is configured to mechanically couple to the pusher member distal coupling member 344. With reference to FIG. 32, the illustrated coupling portion 360*a* comprises a catch configured to releasably hold the raised portion of the pusher member distal coupling member 344. To engage the coupling portions 244, 260, the delivery tube 350 is moved longitudinally relative to the pusher member 344 until the catch is aligned with the raised portion, at which time the raised portion will enter the catch. The catch and raised portion are configured so that the raised portion will exit the catch only upon application of a threshold force. Thus, the pusher member 330 and tube 350 are releasably coupled and longitudinally fixed relative to one another.

With reference again to FIG. 30, the delivery tube 350 comprises a handle 362 disposed adjacent the proximal end 352. The handle 362 preferably comprises two opposing support arms that extend outward from the conical outer surface 350*b* at locations spaced from the weakened portions 356. In the illustrated embodiment, the delivery tube handle 362 comprises two support arms diametrically opposed to each other and disposed generally 90° from the weakened portions 356.

With reference again to FIG. 27, the vascular wound closure assembly 300 is assembled by sliding the distal end 314 of the catheter 310 through the canal 330*a* of the pusher member 330 so that the proximal end 332 of the pusher member 330 preferably abuts the stopper member 316, and so the distal end 314 of the catheter 310 extends out from the distal end 334 of the pusher member 330. The coupling member 320 engages the stop member 316 and pusher member proximal coupling member 342 so that the pusher member 330 is fixed longitudinally to the catheter 310.

The proximal end 352 of the delivery tube 350 is slid over the distal end 314 of the catheter 310 so that the catheter 310 travels through the opening 350d. As the delivery tube 350 is slid proximally over the catheter 310 the coupling portion 360 mechanically engages the distal coupling member 344 of the pusher member 330. As such, the catheter 310, pusher member 330 and delivery tube 350 are fixed longitudinally to one another. Thus, the pusher member and tube move together as a unit. The hemostatic material 270 can be added to the chamber 350d of the delivery tube 350 before or during the assembly process.

With continued reference to FIG. 27, when the apparatus is assembled, the distal end 314 of the catheter 310 extends from the distal end 354 of the delivery tube 350, and the catheter holes 318 preferably are spaced from the distal end 354 a distance at least the same as the width of an artery wall. Preferably, the distance is about 0.5 to 2 millimeters.

To use the apparatus, the assembled device is advanced into the vascular wound "w" in a manner similar to that discussed above in connection with FIGS. 1-4. When the device is positioned so that the distal end 354 of the delivery tube 350 is generally adjacent the wound "w", the coupling member 320 preferably is disengaged from the stop member 316 of the catheter 310 and the proximal coupling member 342 of the pusher member 330. Similarly, the coupling portion 360 of the delivery tube 350 preferably is disengaged from the distal coupling member 344 of the pusher member 330. Accordingly, the pusher member 330 and delivery tube 350 are no longer longitudinally fixed relative to each other.

Figure 33:
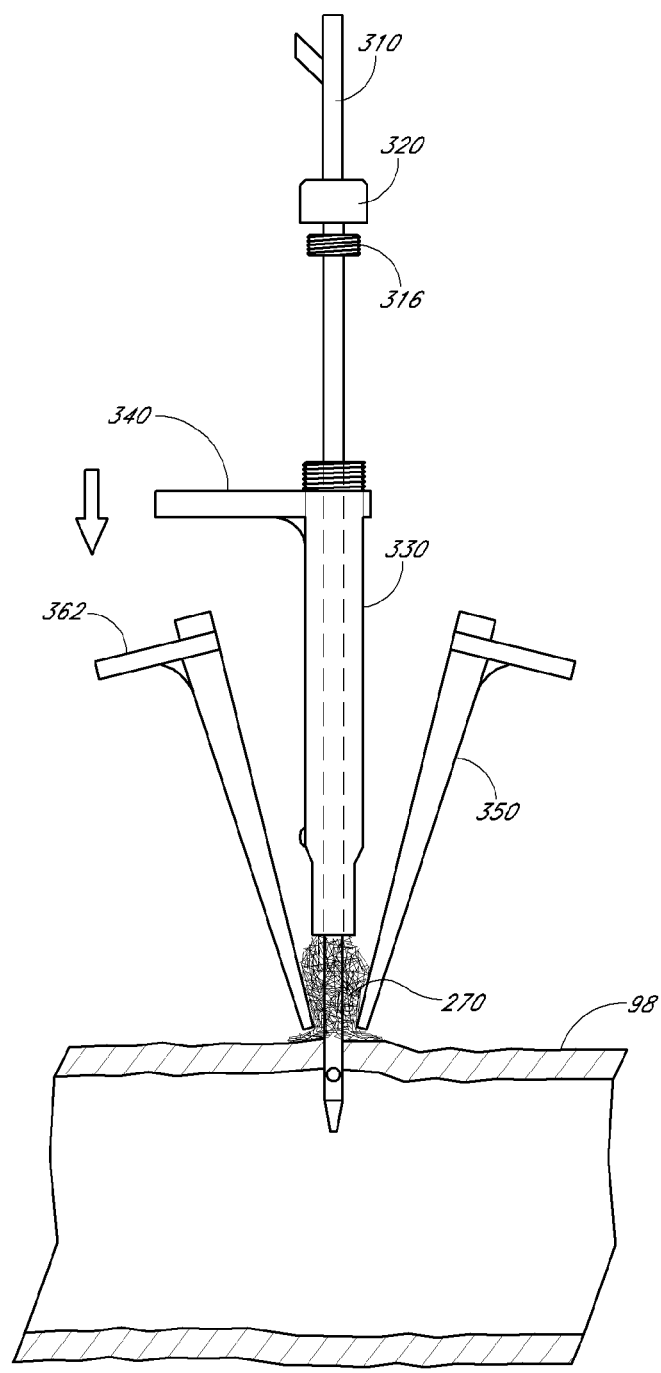
FIG. 33 shows the apparatus of FIG. 22 during use.

With reference next to FIG. 33, the pusher member 330 is then preferably advanced distally into the opening 350d of the delivery tube 350 while the delivery tube 350 is held generally stationary adjacent the wound w. Since the pusher member 330 is generally larger in diameter than the delivery tube 350, the delivery tube 350 breaks along the weakened portions 356 as the pusher member 330 is advanced. In one embodiment, a user grasps the handle 340 of the pusher member 330 and the handle 362 of the delivery tube 350 to drive the pusher member 330 through the delivery tube 350.

As the delivery tube 350 breaks, openings are created so that the hemostatic material 270 is free to exit the chamber. As the pusher member 330 advances, it engages and advances the hemostatic material 270 out of the tube 350 and into contact with the wound "w". Preferably, the broken portions of the delivery tube 350 are removed from the wound location.

As described above in connection with other embodiments, the catheter 310 can be slidably withdrawn through the canal 330a of the pusher member 330. Further, a release rod (not shown) can also be used to provide counter traction to help remove the pusher member 330 from the wound location. For example, the release rod can be slidably inserted through the canal 330a of the pusher member 330 so that it engages the hemostatic material 270 against the wound location. A user can then remove the pusher member 330 without disturbing the hemostatic material 270 because the counter traction provided by the release rod will keep the hemostatic material 270 in place as the pusher member is removed.

In the embodiment discussed above, the coupling members are disengaged before advancing the pusher member relative to the delivery tube. It is to be understood that, in other embodiments, the coupling members can be adapted so that mere application of a force above a threshold force level will defeat the coupling members so as to release the releasably coupled members from one another. Thus, as the user applies force to advance the pusher member, the user simultaneously disengages the coupling members and advances the pusher member.

In another embodiment, the distal coupling member of the pusher member is threaded on its outer surface, and the proximal coupling member of the delivery tube is threaded on its inner surface. As such the pusher member and delivery tube are threadably affixed to each other. In this arrangement, the pusher member is advanced relative to the delivery tube by threading the pusher member. This arrangement allows the user to adjust the distance between the distal ends of the delivery tube and the catheter indicator holes. When the device is positioned so that the delivery tube is adjacent the wound, the pusher member is advanced by continuing to thread the pusher member into the delivery tube as the delivery tube is held in place. As such, the pusher member will advance, and will eventually break the tube at the weakened portions. The pusher member can then be advanced further by using the handles.

In still other embodiments, other types and structures of coupling members can be employed. For example, various releasable locking structures can be employed, such as a J-lock or an L-lock (see FIG. 34). Additionally, in still further embodiments, the coupling members can have still different structure. For example, the coupling member can comprise an adhesive between the pusher member and catheter, which adhesive is configured to be defeated upon application of a threshold force. In yet a further embodiment, the pusher member and catheter are lightly heat bonded or otherwise bonded together. As such, the bond between the pusher member and catheter will be overcome upon application of a threshold force.

FIGS. 35-38 illustrate another embodiment of a vascular closure apparatus 300' having many aspects similar to the embodiment described above with reference to FIGS. 27-33. Where possible, the same reference numerals are used to identify similar elements, but elements of the present embodiment include the appellation "'".

Figure 35:
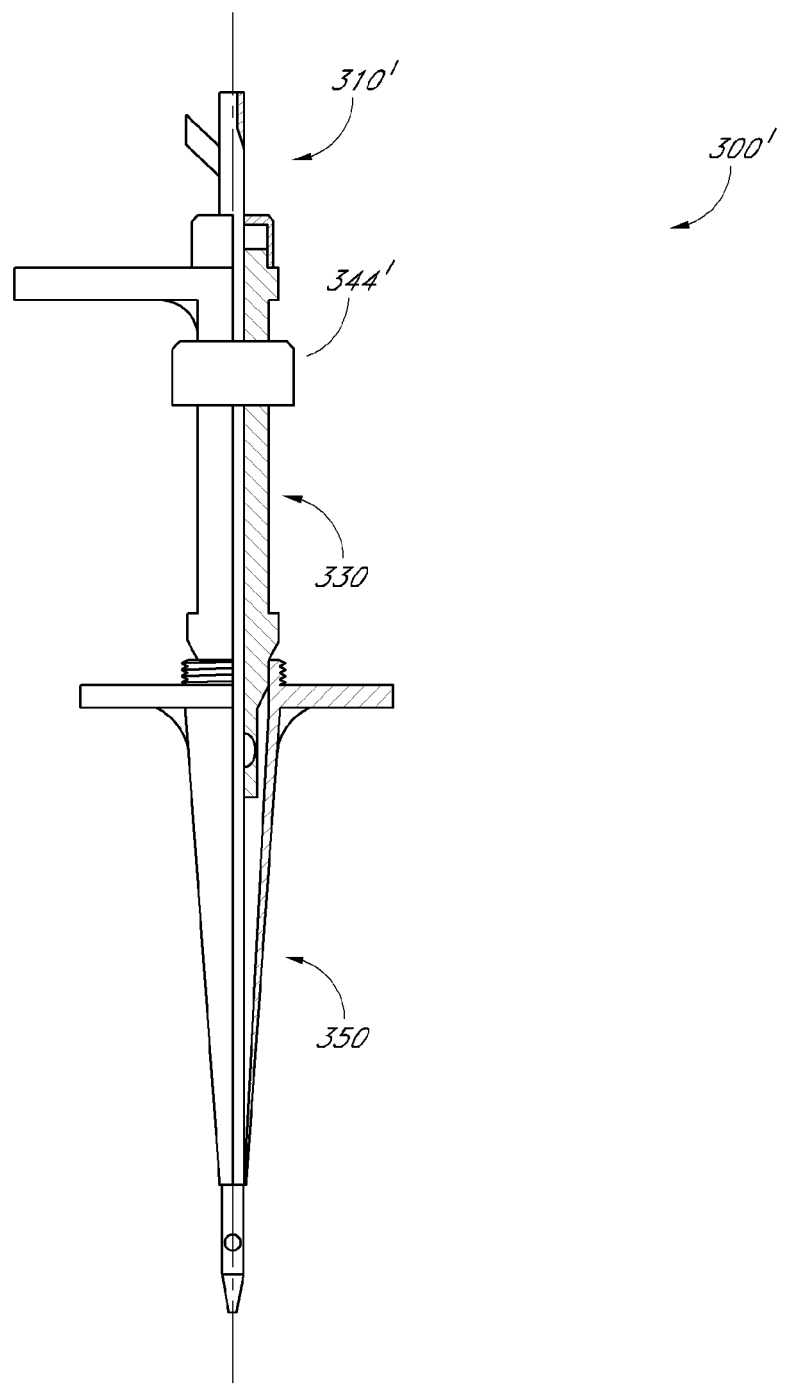
FIG. 35 shows another embodiment of a vascular wound closure apparatus.

With specific reference to FIG. 35, the closure apparatus 300' preferably comprises a catheter 310', a pusher member 330', and a delivery tube 350' releasably connected to each other. Additionally, the apparatus 300' preferably comprises a threaded coupling member 344' slidably disposed about the pusher member 330'.

Figure 36:
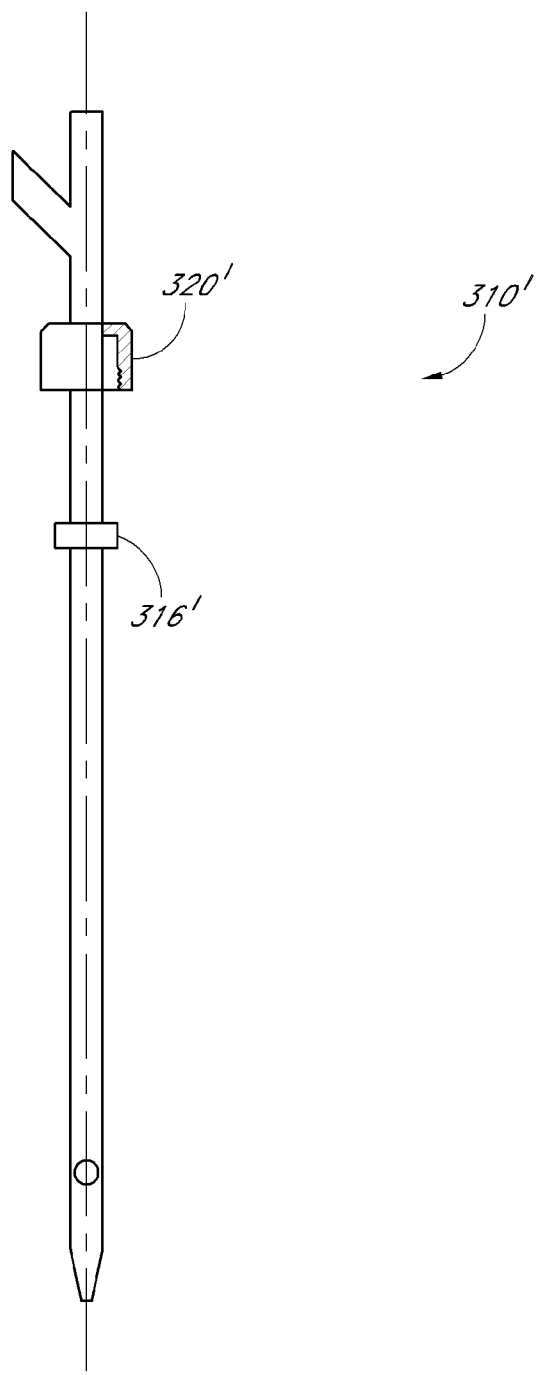
FIG. 36 shows a partially cutaway side view of a catheter according to the embodiment illustrated in FIG. 35.

With specific reference next to FIG. 36, the catheter 310' preferably comprises an unthreaded stop member 316'. Additionally, a coupling member 320' preferably is configured so that a portion of the coupling member is slidable over the stop member 316' so as to enclose it. However, a proximal portion of the coupling member cannot slide over the stop member 316', and thus the stop member limits the distal travel of the coupling member.

Figure 37:
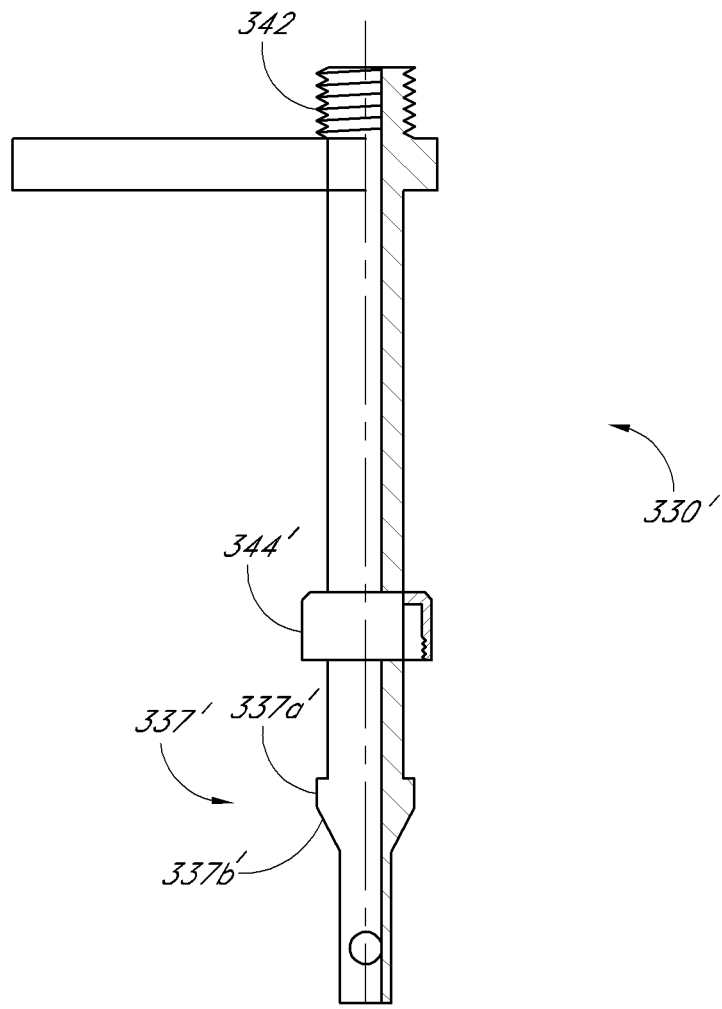
FIG. 37 shows a partially cutaway cross-sectional view of a pusher member according to the embodiment illustrated in FIG. 35.

With reference next to FIGS. 35 and 37, the proximal end 332 of the pusher member 330' is configured to abut against the stop member 316' when the pusher member 330' is slidably disposed on the catheter 310'. The threaded outer surface of the proximal coupling member 342 preferably is configured to mechanically engage the threads of the coupling member 320' when said member 320' is advanced over the proximal end 332 of the pusher member 330'.

The pusher member 330' preferably comprises a transition portion 337' adjacent the distal portion 338. The transition portion 337' preferably comprises a cylindrical raised portion 337a' and a generally conical portion 337b'. The raised portion 337a' comprises an unthreaded outer surface, and preferably is configured to slidably receive a distal portion of the coupling member 344' about and over its outer surface so that the coupling member 344' encloses the raised portion 337a'. A proximal portion of the coupling member 344' cannot slide over the raised portion 337a', and thus the raised portion 337a' limits distal travel of the coupling member 344' over the pusher member 330'.

Figure 38:
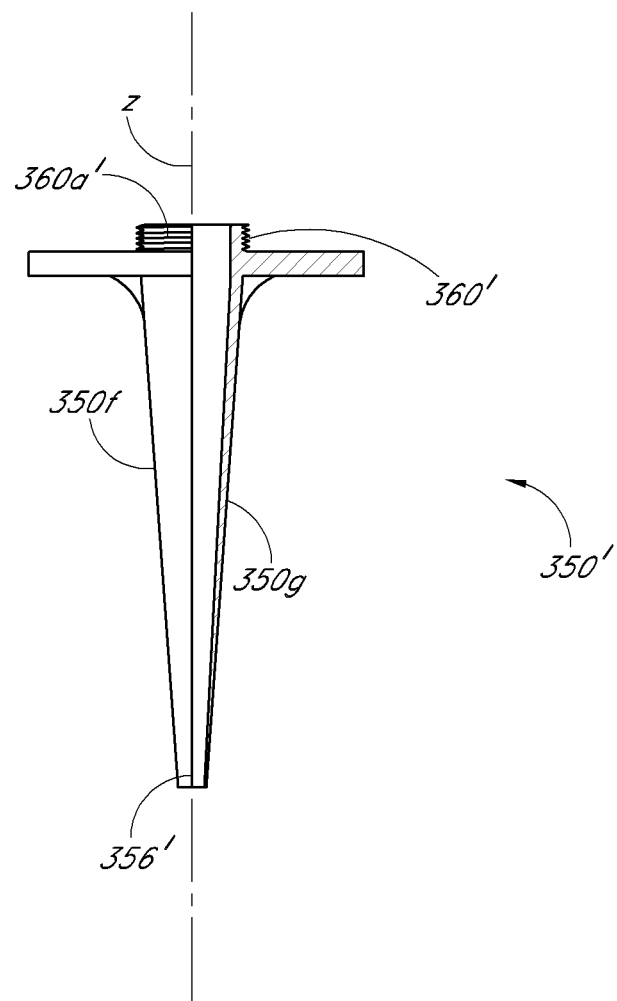
FIG. 38 shows a partially cutaway view of a delivery tube according to the embodiment illustrated in FIG. 35.

With reference to FIGS. 35 and 38, the delivery tube 350' preferably comprises a coupling portion 360' at its proximal end 352. The coupling portion 360' preferably includes a threaded outer surface 360a' configured to mechanically engage the coupling member 344'. In one preferred embodiment, the delivery tube 350' comprises weakened portions 356, as previously discussed. In another preferred embodiment, the body 350a' of the delivery tube 350' comprises two separate halves 350f, 350g configured to abut against each other about an axis "z" and be held in a generally fixed position relative to each other when the coupling member 344' is threaded onto the coupling portion 360'. In yet another preferred embodiment, the delivery tube 350' comprises a body 350a' with two halves 350f, 350g joined at the proximal end 352 of the delivery tube 350' by weakened portions 356'. In another embodiment, the two halves are joined by an elastic member which helps hold the halves together before the hemostatic material is deployed.

With reference again to FIG. 35, the vascular closure apparatus 300' preferably is assembled so that the catheter 310', the pusher member 330', and the delivery tube 350' are releasably coupled by the coupling members so as to be fixed relative to each other. For example, the catheter 310' is slidably inserted into the pusher member 330' until the stopper member 316' abuts against the proximal end 332 of the pusher member 330'. The coupling member 320' is then slid over the stopper member 316' and threaded onto the proximal coupling member 342 of the pusher member 330'. The delivery tube 350' is similarly slid over the catheter 310' and pusher member 330' until the proximal end 352 of the delivery tube 350' abuts against the transition portion 337', wherein the delivery tube 350' preferably encloses the hemostatic material 270 therein. The coupling member 344' is then slid over the raised portion 337a' and threadably engages the coupling portion 360'.

As previously discussed, once the device is in place adjacent the wound "w", the coupling members 344', 320' are disengaged so that the pusher member 330' is uncoupled from the catheter 310' and the delivery tube 350'. The user advances the pusher member 330' into the delivery tube 350' to deform the tube and engage and advance the hemostatic material 270 adjacent the wound "w".

In the embodiments just discussed, the delivery tube is configured to break when the pusher member is advanced. In other embodiments, the delivery tube may not break, but deforms sufficiently so that material within the tube can be dispatched therefrom. For example, at least a portion of the tube may be formed of an elastic material, such as silicone, so that the pusher member deforms the tube and forces material out of the tube and adjacent the wound. Additionally, in one embodiment wherein the tube is formed of an elastic material, the tube does not necessarily include a weakened portion.

In accordance with another embodiment, a vascular wound closure apparatus have features as discussed above in connection with FIG. 22-33 or 35-38 is provided in a kit for use by a clinician. In this embodiment, the apparatus is formed of a disposable, yet suitable material, such as a medical grade plastic, and is assembled and loaded so that the members are releasably coupled to one another and hemostatic material is disposed in the delivery tube. The apparatus is in a sterilized and preferably is disposed within a closed, sterilized container (not shown) which is configured to be opened in a sterile environment such as an operating room or catheter lab.

Although this invention has been disclosed in the context of certain preferred embodiments and examples, it will be understood by those skilled in the art that the present invention extends beyond the specifically-disclosed embodiments to other alternative embodiments and/or uses of the invention and obvious modifications and equivalents thereof. In addition, while a number of variations have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed modular arrangement and method. Thus, it is intended that the scope of the present invention should not be limited by the particular disclosed embodiments described above, but should be determined only by a fair reading of the claims that follow.

What is claimed is:

1. An assembly for closing a vascular wound, comprising:
   a hemostatic material;
   a delivery tube configured to accommodate the hemostatic material therewithin, the delivery tube having a proximal end and a distal end;
   an apparatus configured to position the distal end of the delivery tube adjacent a vascular wound;
   a pusher member having a distal portion configured to fit at least partially through the proximal end of the delivery tube, wherein a portion of the pusher member has a diameter larger than a diameter of at least a portion of the delivery tube, wherein the pusher member defines a canal that extends from a proximal end of the pusher member to a distal end of the pusher member, wherein the pusher member comprises a distal coupling member disposed proximal to a transition portion adjacent to the distal portion, wherein the distal coupling member comprises a generally hemispherical raised portion;
   a catheter having a tapered distal portion and at least one catheter hole proximal the tapered distal portion of the catheter, wherein the canal is configured to slidably receive the catheter therethrough;
   a stop member disposed about a surface of the catheter; and
   a coupling member movably disposed about the catheter and configured to engage the stop member and engage a proximal coupling member on the pusher member to releasably couple the catheter and pusher member.

2. The assembly of claim 1, wherein the catheter is configured to extend through the delivery tube.

3. The assembly of claim 2, wherein the hemostatic material is configured to be disposed between the catheter and the delivery tube.

4. The assembly of claim 1, wherein the distal coupling member is configured to releasably couple the pusher member and the delivery tube.

5. The assembly of claim 1, further comprising means for releasably coupling the delivery tube, the apparatus, and the pusher member in fixed relation to one another.

6. The assembly of claim 1, wherein the delivery tube is generally conical.

7. The assembly of claim 1, wherein at least one portion of the delivery tube is a weakened portion.

8. The assembly of claim 7, wherein the weakened portion is a wall section of reduced thickness.

9. The assembly of claim 7, wherein the weakened portion is a scored wall section.

10. The assembly of claim 1, wherein the delivery tube comprises two separate halves coupled together.

11. The assembly of claim 1, wherein the delivery tube comprises an elastic material.

12. The assembly of claim 1, wherein the canal has a circular cross-section with a diameter larger than a diameter of the catheter's surface, and wherein the canal is not large enough to fit over the stop member, such that the pusher member cannot be moved proximally over the catheter beyond the stop member.

13. The assembly of claim 1, wherein the pusher member comprises one or more handles situated near the proximal end of the pusher member.

14. The assembly of claim 1, wherein the proximal coupling member comprises threads on its outer surface sized and configured to engage threads of the coupling member, and wherein the coupling member is configured to engage both the stop member and the proximal coupling member so as to selectively hold the pusher member longitudinally fixed relative to the catheter.

15. A method for closing a vascular wound comprising:
   providing the assembly of claim 1;
   positioning the distal end of the delivery tube adjacent the vascular wound; and
   moving the pusher member distally relative to the delivery tube so that at least a portion of the delivery tube deforms so that the hemostatic material is dispatched from the delivery tube.

16. The method of claim 15, wherein the delivery tube breaks when the pusher member is moved distally.

* * * * *